US006300098B1

(12) United States Patent
Norris et al.

(10) Patent No.: US 6,300,098 B1

(45) Date of Patent: Oct. 9, 2001

(54) HUMAN SIGNAL TRANSDUCTION SERINE/ THREONINE KINASE

(75) Inventors: Tyrrell Errick Norris, New Castle, DE (US); William Craig Moore, West Grove; David Shay Silberstein, Kenneth Square, both of PA (US)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/468,442

(22) Filed: Dec. 21, 1999

Related U.S. Application Data

(60) Division of application No. 09/340,993, filed on Jun. 25, 1999, now Pat. No. 6,034,228, which is a continuation-in-part of application No. 09/211,930, filed on Dec. 15, 1998, now Pat. No. 5,962,265.

(30) Foreign Application Priority Data

Dec. 19, 1997 (GB) .......................................... G13 9726851

(51) Int. Cl.[7] .......................... C12N 9/100; C12N 15/63; C07K 5/00; A61K 38/43; C12P 21/06

(52) U.S. Cl. ........................... 435/69.1; 424/94.1; 435/6; 435/320.1; 435/325; 435/183; 530/350

(58) Field of Search ................................ 536/23.1, 24.3, 536/24.33, 24.5; 435/6, 69.1, 325, 375

(56) References Cited

FOREIGN PATENT DOCUMENTS

WO97/42212 11/1997 (GB) .

OTHER PUBLICATIONS

Andrea D. Branch, A good antisense molecule is hard to find, TIBS, 47–48, Feb. 1998.*

Stanley Crooke, Antisense Research and Applications, Chapter 1, Basic Principles of Antisense Therapeutics, Springer–Verlag Press, Berlin, Heidelberg, New York, p. 3, Jul. 1998.*

W. French Anderson, Human gene therapy, Nature, vol. 392, pp. 25–30, Apr. 1998.*

Stuart Orkin & Arno Motulsky, Report and Recommendations of the panel to assess the NIH investment in research on gene therapy. NIH web page (http://www.nig.gov), pp. 1–23, Feb. 1998.*

Pombo, Celia M. et al., Activation of a human Ste20–like kinase byOxidant Stress Defines a Novel Stress Response Pathway, The Embo Journal, 15/17:4537 (1996).

Friedemann Kiefer [12], et al., HPK1, A Hematopoietic Protein Kinase Activating the SAPK/JNK Pathway, The Embo Journal, 15/24:7013 (1996).

Creasy, Caretha L., et al., Cloning and Characterization of a Member of the MST Subfamily of Ste20–Like Kinases, Gene, 167:303 (1995).

Hu, Mickey C.–T.,et al., Human HPK1, A Novel Human Hematopoietic Progenitor Kinase That Activates the JNK/ SAPK Kinase Cascade, Genes and Development, 10:2251 (1996).

Creasy, Caretha L., et al., Cloning and Characterization of a Human Protein Kinase with Homology to Ste20, The Journal of Biological Chemistry, 270:21695 (1995).

Pombo, Cella M. et al., Activation of the SAPK Pathway by the Human STE20 Homologue Germinal Centre Kinase, Nature, 377:750 (1995).

Creasy, Caretha L., et al., The Ste20–like Protein Kinase, Mst1, Dimerizes and Contains and Inhibitory Domain, The Journal of Biological Chemistry, 271:21049 (1996).

Hanks, Steven K.,et al., Protein Kinases 6—The Eukaryotic Protein Kinase Superfamily:Kinase (Catalytic) Domain Structure and Classification[1], The FASEB Journal, 9:578 (1995).

Hanks, Steven K., et al., The Protein Kinase Family: Conserved Features and Deduced Phylogeny of the Catalytic Domains, Science 241:42 (1988).

Ravichandran, K.S., et al., Coreceptor and Adapter Proteins in T–Cell Signaling, Annals of the New York Academy of Sciences, p. 117 (1995).

Tonks, N.K., Protein Tyrosine Phosphatases and the Control of Cellular Signaling Responses, Advances in Pharmacology, 36:91 (1996).

Polla, B. S., et al., Stress Proteins in Inflammation, Stress Inducible Cellular Responses, p. 375 (1996).

Cobb, Melanie H., et al., Structural Analysis of the MAP Kinase ERK2 and Studies of MAP Kinase Regulatory Pathways, Advances in Pharmacology, 16:49 (1996).

Cohen, Philip, Dissection of Protein Kinase Cascades That Mediate Cellular Response to Cytokines and Cellular Stress, Advances in Pharmacology, 36:15 (1996).

Welch, William J., et al., The Stress Response and the Immune System, Inflammation:Basic Principles and Clinical Correlates 41:841 (1992).

Holbrook, N.J., et al. Signaling Events Controlling the Molecular Response to Genotoxic Stress, Stress Inducible Cellular Responses, 273 (1996).

Schinkmann, K., et al., Cloning and Characterizaton of a human STE20–like Protein Kinase with Unusyual Cofactor Requirements, J. Biol. Chem., 272(45):28695 (1997).

Barnes, P. J., et al., NF–KB: A Pivatol Role in Asthma and a New Target for Tharapy, TIPS, 18:46 (1997).

* cited by examiner

*Primary Examiner*—Robert A. Schwartzman
*Assistant Examiner*—Janet Epps

(57) ABSTRACT

An isolated and purified human Ste20-like serine/threonine signal transduction kinase is described. A cDNA sequence which encodes the native signal transduction molecule is disclosed as well as the structural coding region and the amino acid residue sequence. Methods are provided which employ the sequences to identify compounds that modulate the biological and/or pharmacological activity of the transduction molecule and hence regulate cell physiology. Biologically-effective antisense molecules, as well as dominant negative mutant versions of the biomolecule are described which are suitable for therapeutic use. The invention is also drawn toward the diagnosis, prevention, and treatment of pathophysiological disorders mediated by the signal transduction molecule.

3 Claims, No Drawings

SEQUENCE LISTING

```
<160> NUMBER OF SEQ ID NOS: 14

<210> SEQ ID NO 1
<211> LENGTH: 3201
<212> TYPE: DNA
<213> ORGANISM: Homo sapiens

<400> SEQUENCE: 1
```

-continued

```
taacagccca cctcctagcc ccgggctacg cgccgccagc ccagtaaccc cacttttgtg      60
tgtcctccca ggccccgatc gaaaagcctg ggagggccgc cgaactaccc ccggagggag     120
gagccagtcc gaacccaagg cgccaccgcc gcagaagcgg agcgaggcag cattcgcctc     180
catggcccac tcgccggtgg ctgtccaagt gcctgggatg cagaataaca tagctgatcc     240
agaagaactg ttcacaaaat tagagcgcat tgggaaaggc tcatttgggg aagttttcaa     300
aggaattgat aaccgtaccc agcaagtcgt tgctattaaa atcatagacc ttgaggaagc     360
cgaagatgaa atagaagaca ttcagcaaga aataactgtc ttgagtcaat gtgacagctc     420
atatgtaaca aaatactatg ggtcatattt aaaggggtct aaattatgga taataatgga     480
atacctgggc ggtggttcag cactggatct tcttcgagct ggtccatttg atgagttcca     540
gattgctacc atgctaaagg aaattttaaa aggtctggac tatctgcatt cagaaaagaa     600
aattcaccga gacataaaag ctgccaatgt cttgctctca gaacaaggag atgttaaact     660
tgctgatttt ggagttgctg gtcagctgac agatacacag attaaaagaa ataccttttgt    720
gggaactcca ttttggatgg ctcctgaagt tattcaacag tcagcttatg actcaaaagc     780
tgacatttgg tcattgggaa ttactgctat tgaactagcc aagggagagc cacctaactc     840
cgatatgcat ccaatgagag ttctgtttct tattcccaaa aacaatcctc caactcttgt     900
tggagacttt actaagtctt ttaaggagtt tattgatgct tgcctgaaca aagatccatc     960
atttcgtcct acagcaaaag aacttctgaa acacaaattc attgtaaaaa attcaaagaa    1020
gacttcttat ctgactgaac tgatagatcg ttttaagaga tggaaggcag aaggacacag    1080
tgatgatgaa tctgattccg agggctctga ttcggaatct accagcaggg aaaacaatac    1140
tcatcctgaa tggagcttta ccaccgtacg aaagaagcct gatccaaaga aagtacagaa    1200
tggggcagag caagatcttg tgcaaaccyt gagttgtttg tctatgataa tcacacctgc    1260
atttgctgaa cttaaacagc aggacgagaa taacgctagc aggaatcagg cgattgaaga    1320
actcgagaaa agtattgctg tggctgaagc cgcctgtccc ggcatcacag ataaaatggt    1380
gaagaaacta attgaaaaat ttcaaaagtg ttcagcagac gaatccccct aagaaactta    1440
ttattggctt ctgtttcata tggacccaga gagccccacc aaacctacgt caagattaac    1500
aatgcttaac ccatgagctc catgtgcctt ttggatcttt gcaacactga agatttggaa    1560
gaagctatta aactattttg tgatggcgtt tatcatttta tattttgaaa ggattatttt    1620
gtaaggaata acttttaata ctatagtttc acctgtattc tagtaaatgt tgagacaccg    1680
ttttgctttt aagtatccct atttcttaag ttacgaggat gaataccttt cacattttga    1740
tctttagttg actctacagt catgaaacat acaggtcttt caaagtcatt ctcaatattc    1800
agcttttgta aattatcaag cttcaaaaag ctttttttta aaaaaaaaaa catgcatatt    1860
ctaaaaatga ctattgggtg gggaggtgta aataagtcat accttcttaa aacagaaaat    1920
ttaagtaaag tcttttaaat gaaacctgta aaagtattga ctcttctacc aagttggtat    1980
gatattccag gcagctcaat gattatcaca tttgagaccc tgtgtttgaa gcatttacag    2040
gcaatgtaca gcaacagagg tacctcttgg tgtatagtat ttacattctc ttttaggtag    2100
aagaggcaat tttaccctta tttcacatgg ttagaaattt aaagcaagat catttaccca    2160
aggataggtg tttggtaatg ttgaaggagt tagtctggct tcatgtttta catcttcaac    2220
taaaatccca tactatctgc ttggatttgg agagccaaaa aataaagctg attgtcatgt    2280
gattaaatat ctgatcaaca ggtatgaata taacttaaat cagcatattt ttgccatggt    2340
```

-continued

```
aataaattgt cctataaact atttatatat ttttgttctt cataattatc actaataagc   2400

atcagtttgt tgtttttaaa aggatattta agtgagcatt ttctagttca tatgaaaata   2460

accatagtac aggatgattt ctgtccacac aaaggttaaa ttagattgca cagttaattt   2520

tcacttatat ttatggtact attatgtggg tgatgccttt ttcttttaag cccagtacat   2580

atattatgcc tgcctaagtt ctgaactggg gctgtatttc agtagttgta gaattattga   2640

tatttagttt tgatagctaa tgtttaattg tttggatctg cacagtttgg tttttgcaca   2700

aaagtcattt aaaaaaatct gagtaattgt caaatattaa aagaaagata ttcttcctgt   2760

aaggaataca gtttttagtc aaagtggcca ttacatcctc tttttaattt acataataca   2820

gatacttgag aaagttgttg tggtgttgta tgccaagaaa attcttttta ttggtgccta   2880

tattgtaaca attattttta atgcattgta ttttgaagta acggttcagt taaatttttc   2940

acctgctgtg taactgaaac acaattacag tttataatca tctgtagaag tctggagata   3000

attttgcaac tcatgttatg ggttaaatga atatttttgt aaaagtaaaa gcaacaaatt   3060

tataaattga ttatttgaaa ctttacaaca caattgcatc ccaaatacaa attgtattgc   3120

ttattcatta tagctattcg tcctgtaatc tgtttctagg tgaagcatac tccagtgttt   3180

taggggtttt gaaaataaat a                                             3201
```

```
<210> SEQ ID NO 2
<211> LENGTH: 1251
<212> TYPE: DNA
<213> ORGANISM: Homo sapiens

<400> SEQUENCE: 2

atggcccact cgccggtggc tgtccaagtg cctgggatgc agaataacat agctgatcca     60

gaagaactgt tcacaaaatt agagcgcatt gggaaaggct catttgggga agttttcaaa    120

ggaattgata accgtaccca gcaagtcgtt gctattaaaa tcatagacct tgaggaagcc    180

gaagatgaaa tagaagacat tcagcaagaa ataactgtct tgagtcaatg tgacagctca    240

tatgtaacaa aatactatgg gtcatattta aaggggtcta aattatggat aataatggaa    300

tacctgggcg gtggttcagc actggatctt cttcgagctg gtccatttga tgagttccag    360

attgctacca tgctaaagga aattttaaaa ggtctggact atctgcattc agaaaagaaa    420

attcaccgag acataaaagc tgccaatgtc ttgctctcag aacaaggaga tgttaaactt    480

gctgattttg gagttgctgg tcagctgaca gatacacaga ttaaaagaaa tacctttgtg    540

ggaactccat tttggatggc tcctgaagtt attcaacagt cagcttatga ctcaaaagct    600

gacatttggt cattgggaat tactgctatt gaactagcca agggagagcc acctaactcc    660

gatatgcatc caatgagagt tctgtttctt attcccaaaa acaatcctcc aactcttgtt    720

ggagacttta ctaagtcttt taaggagttt attgatgctt gcctgaacaa agatccatca    780

tttcgtccta cagcaaaaga acttctgaaa cacaaattca ttgtaaaaaa ttcaaagaag    840

acttcttatc tgactgaact gatagatcgt tttaagagat ggaaggcaga aggacacagt    900

gatgatgaat ctgattccga gggctctgat tcggaatcta ccagcaggga aaacaatact    960

catcctgaat ggagctttac caccgtacga aagaagcctg atccaaagaa agtacagaat   1020

ggggcagagc aagatcttgt gcaaaccctg agttgtttgt ctatgataat cacacctgca   1080

tttgctgaac ttaaacagca ggacgagaat aacgctagca ggaatcaggc gattgaagaa   1140

ctcgagaaaa gtattgctgt ggctgaagcc gcctgtcccg gcatcacaga taaaatggtg   1200

aagaaactaa ttgaaaaatt tcaaaagtgt tcagcagacg aatcccccta a             1251
```

-continued

<210> SEQ ID NO 3
<211> LENGTH: 416
<212> TYPE: PRT
<213> ORGANISM: Homo sapiens

<400> SEQUENCE: 3

```
Met Ala His Ser Pro Val Ala Val Gln Val Pro Gly Met Gln Asn Asn
 1               5                  10                  15

Ile Ala Asp Pro Glu Glu Leu Phe Thr Lys Leu Glu Arg Ile Gly Lys
            20                  25                  30

Gly Ser Phe Gly Glu Val Phe Lys Gly Ile Asp Asn Arg Thr Gln Gln
        35                  40                  45

Val Val Ala Ile Lys Ile Ile Asp Leu Glu Glu Ala Glu Asp Glu Ile
    50                  55                  60

Glu Asp Ile Gln Gln Glu Ile Thr Val Leu Ser Gln Cys Asp Ser Ser
65                  70                  75                  80

Tyr Val Thr Lys Tyr Tyr Gly Ser Tyr Leu Lys Gly Ser Lys Leu Trp
                85                  90                  95

Ile Ile Met Glu Tyr Leu Gly Gly Gly Ser Ala Leu Asp Leu Leu Arg
            100                 105                 110

Ala Gly Pro Phe Asp Glu Phe Gln Ile Ala Thr Met Leu Lys Glu Ile
        115                 120                 125

Leu Lys Gly Leu Asp Tyr Leu His Ser Glu Lys Lys Ile His Arg Asp
    130                 135                 140

Ile Lys Ala Ala Asn Val Leu Leu Ser Glu Gln Gly Asp Val Lys Leu
145                 150                 155                 160

Ala Asp Phe Gly Val Ala Gly Gln Leu Thr Asp Thr Gln Ile Lys Arg
                165                 170                 175

Asn Thr Phe Val Gly Thr Pro Phe Trp Met Ala Pro Glu Val Ile Gln
            180                 185                 190

Gln Ser Ala Tyr Asp Ser Lys Ala Asp Ile Trp Ser Leu Gly Ile Thr
        195                 200                 205

Ala Ile Glu Leu Ala Lys Gly Glu Pro Pro Asn Ser Asp Met His Pro
    210                 215                 220

Met Arg Val Leu Phe Leu Ile Pro Lys Asn Asn Pro Pro Thr Leu Val
225                 230                 235                 240

Gly Asp Phe Thr Lys Ser Phe Lys Glu Phe Ile Asp Ala Cys Leu Asn
                245                 250                 255

Lys Asp Pro Ser Phe Arg Pro Thr Ala Lys Glu Leu Leu Lys His Lys
            260                 265                 270

Phe Ile Val Lys Asn Ser Lys Lys Thr Ser Tyr Leu Thr Glu Leu Ile
        275                 280                 285

Asp Arg Phe Lys Arg Trp Lys Ala Glu Gly His Ser Asp Asp Glu Ser
    290                 295                 300

Asp Ser Glu Gly Ser Asp Ser Glu Ser Thr Ser Arg Glu Asn Asn Thr
305                 310                 315                 320

His Pro Glu Trp Ser Phe Thr Thr Val Arg Lys Lys Pro Asp Pro Lys
                325                 330                 335

Lys Val Gln Asn Gly Ala Glu Gln Asp Leu Val Gln Thr Leu Ser Cys
            340                 345                 350

Leu Ser Met Ile Ile Thr Pro Ala Phe Ala Glu Leu Lys Gln Gln Asp
        355                 360                 365

Glu Asn Asn Ala Ser Arg Asn Gln Ala Ile Glu Glu Leu Glu Lys Ser
```

-continued

```
    370                 375                 380

Ile Ala Val Ala Glu Ala Ala Cys Pro Gly Ile Thr Asp Lys Met Val
385                 390                 395                 400

Lys Lys Leu Ile Glu Lys Phe Gln Lys Cys Ser Ala Asp Glu Ser Pro
                405                 410                 415


<210> SEQ ID NO 4
<211> LENGTH: 426
<212> TYPE: PRT
<213> ORGANISM: Homo sapiens

<400> SEQUENCE: 4

Met Ala His Leu Arg Gly Phe Ala Asn Gln His Ser Arg Val Asp Pro
 1               5                  10                  15

Glu Glu Leu Phe Thr Lys Leu Asp Arg Ile Gly Lys Gly Ser Phe Gly
            20                  25                  30

Glu Val Tyr Lys Gly Ile Asp Asn His Thr Lys Glu Val Val Ala Ile
        35                  40                  45

Lys Ile Ile Asp Leu Glu Glu Ala Glu Asp Glu Ile Glu Asp Ile Gln
    50                  55                  60

Gln Glu Ile Thr Val Leu Ser Gln Cys Asp Ser Pro Tyr Ile Thr Arg
65                  70                  75                  80

Tyr Phe Gly Ser Tyr Leu Lys Ser Thr Lys Leu Trp Ile Ile Met Glu
                85                  90                  95

Tyr Leu Gly Gly Gly Ser Ala Leu Asp Leu Leu Lys Pro Gly Pro Leu
            100                 105                 110

Glu Glu Thr Tyr Ile Ala Thr Ile Leu Arg Glu Ile Leu Lys Gly Leu
        115                 120                 125

Asp Tyr Leu His Ser Glu Arg Lys Ile His Arg Asp Ile Lys Ala Ala
    130                 135                 140

Asn Val Leu Leu Ser Glu Gln Gly Asp Val Lys Leu Ala Asp Phe Gly
145                 150                 155                 160

Val Ala Gly Gln Leu Thr Asp Thr Gln Ile Lys Arg Asn Thr Phe Val
                165                 170                 175

Gly Thr Pro Phe Trp Met Ala Pro Glu Val Ile Lys Gln Ser Ala Tyr
            180                 185                 190

Asp Phe Lys Ala Asp Ile Trp Ser Leu Gly Ile Thr Ala Ile Glu Leu
        195                 200                 205

Ala Lys Gly Glu Pro Pro Asn Ser Asp Leu His Pro Met Arg Val Leu
    210                 215                 220

Phe Leu Ile Pro Lys Asn Ser Pro Pro Thr Leu Glu Gly Gln His Ser
225                 230                 235                 240

Lys Pro Phe Lys Glu Phe Val Glu Ala Cys Leu Asn Lys Asp Pro Arg
                245                 250                 255

Phe Arg Pro Thr Ala Lys Glu Leu Leu Lys His Lys Phe Ile Thr Arg
            260                 265                 270

Tyr Thr Lys Lys Thr Ser Phe Leu Thr Glu Leu Ile Asp Arg Tyr Lys
        275                 280                 285

Arg Trp Lys Ser Glu Gly His Gly Glu Glu Ser Ser Ser Glu Asp Ser
    290                 295                 300

Asp Ile Asp Gly Glu Ala Glu Asp Gly Glu Gln Gly Pro Ile Trp Thr
305                 310                 315                 320

Phe Pro Pro Thr Ile Arg Pro Ser Pro His Ser Lys Leu His Lys Gly
                325                 330                 335
```

-continued

```
Thr Ala Leu His Ser Ser Gln Lys Pro Ala Asp Ala Val Lys Arg Gln
            340                 345                 350

Pro Arg Ser Gln Cys Leu Ser Thr Leu Val Arg Pro Val Phe Gly Glu
        355                 360                 365

Leu Lys Glu Lys His Lys Gln Ser Gly Gly Ser Val Gly Ala Leu Glu
    370                 375                 380

Glu Leu Glu Asn Ala Phe Ser Leu Ala Glu Glu Ser Cys Pro Gly Ile
385                 390                 395                 400

Ser Asp Lys Leu Met Val His Leu Val Glu Arg Val Gln Arg Phe Ser
                405                 410                 415

His Asn Arg Asn His Leu Thr Ser Thr Arg
            420                 425


<210> SEQ ID NO 5
<211> LENGTH: 431
<212> TYPE: PRT
<213> ORGANISM: Homo sapiens

<400> SEQUENCE: 5

Met Ala His Ser Pro Val Gln Ser Gly Leu Pro Gly Met Gln Asn Leu
 1               5                  10                  15

Lys Ala Asp Pro Glu Glu Leu Phe Thr Lys Leu Glu Lys Ile Gly Lys
            20                  25                  30

Gly Ser Phe Gly Glu Val Phe Lys Gly Ile Asp Asn Arg Thr Gln Lys
        35                  40                  45

Val Val Ala Ile Lys Ile Ile Asp Leu Glu Glu Ala Glu Asp Glu Ile
    50                  55                  60

Glu Asp Ile Gln Gln Glu Ile Thr Val Leu Ser Gln Cys Asp Ser Pro
65                  70                  75                  80

Tyr Val Thr Lys Tyr Tyr Gly Ser Tyr Leu Lys Asp Thr Lys Leu Trp
                85                  90                  95

Ile Ile Met Glu Tyr Leu Gly Gly Gly Ser Ala Leu Asp Leu Leu Glu
            100                 105                 110

Pro Gly Pro Leu Asp Glu Thr Gln Ile Ala Thr Ile Leu Arg Glu Ile
        115                 120                 125

Leu Lys Gly Leu Asp Tyr Leu His Ser Glu Lys Lys Ile His Arg Asp
    130                 135                 140

Ile Lys Ala Ala Asn Val Leu Leu Ser Glu His Gly Glu Val Lys Leu
145                 150                 155                 160

Ala Asp Phe Gly Val Ala Gly Gln Leu Thr Asp Thr Gln Ile Lys Arg
                165                 170                 175

Asn Thr Phe Val Gly Thr Pro Phe Trp Met Ala Pro Glu Val Ile Lys
            180                 185                 190

Gln Ser Ala Tyr Asp Ser Lys Ala Asp Ile Trp Ser Leu Gly Ile Thr
        195                 200                 205

Ala Ile Glu Leu Ala Arg Gly Glu Pro Pro His Ser Glu Leu His Pro
    210                 215                 220

Met Lys Val Leu Phe Leu Ile Pro Lys Asn Asn Pro Pro Thr Leu Glu
225                 230                 235                 240

Gly Asn Tyr Ser Lys Pro Leu Lys Glu Phe Val Glu Ala Cys Leu Asn
                245                 250                 255

Lys Glu Pro Ser Phe Arg Pro Thr Ala Lys Glu Leu Leu Lys His Lys
            260                 265                 270

Phe Ile Leu Arg Asn Ala Lys Lys Thr Ser Tyr Leu Thr Glu Leu Ile
        275                 280                 285
```

-continued

```
Asp Arg Tyr Lys Arg Trp Lys Ala Glu Gln Ser His Asp Asp Ser Ser
    290                 295                 300

Ser Glu Asp Ser Asp Ala Glu Thr Asp Gly Gln Ala Ser Gly Gly Ser
305                 310                 315                 320

Asp Ser Gly Asp Trp Ile Phe Thr Ile Arg Glu Lys Asp Pro Lys Asn
                325                 330                 335

Leu Glu Asn Gly Ala Leu Gln Pro Ser Asp Leu Asp Arg Asn Lys Met
            340                 345                 350

Lys Asp Ile Pro Lys Arg Pro Phe Ser Gln Cys Leu Ser Thr Ile Ile
        355                 360                 365

Ser Pro Leu Phe Ala Glu Leu Lys Glu Lys Ser Gln Ala Cys Gly Gly
    370                 375                 380

Asn Leu Gly Ser Ile Glu Glu Leu Arg Gly Ala Ile Tyr Leu Ala Glu
385                 390                 395                 400

Glu Val Cys Pro Gly Ile Ser Asp Thr Met Val Ala Gln Leu Val Gln
                405                 410                 415

Arg Leu Gln Arg Tyr Ser Leu Ser Gly Gly Gly Thr Ser Ser His
            420                 425                 430


<210> SEQ ID NO 6
<211> LENGTH: 24
<212> TYPE: DNA
<213> ORGANISM: Artificial Sequence
<220> FEATURE:
<223> OTHER INFORMATION: PCR primer

<400> SEQUENCE: 6

gcctccatgg cccactcgcc ggtg                                              24


<210> SEQ ID NO 7
<211> LENGTH: 25
<212> TYPE: DNA
<213> ORGANISM: Artificial Sequence
<220> FEATURE:
<223> OTHER INFORMATION: PCR primer

<400> SEQUENCE: 7

ggcacatgga gctcatgggt taagc                                             25


<210> SEQ ID NO 8
<211> LENGTH: 1353
<212> TYPE: DNA
<213> ORGANISM: Homo sapiens

<400> SEQUENCE: 8

gcctccatgg cccactcgcc ggtggctgtc caagtgcctg ggatgcagaa taacatagct      60

gatccagaag aactgttcac aaaattagag cgcattggga aaggctcatt tggggaagtt     120

ttcaaaggaa ttgataaccg tacccagcaa gtcgttgcta ttaaaatcat agaccttgag     180

gaagccgaag atgaaataga agacattcag caagaaataa ctgtcttgag tcaatgtgac     240

agctcatatg taacaaaata ctatgggtca tatttaaagg ggtctaaatt atggataata     300

atggaatacc tgggcggtgg ttcagcactg gatcttcttc gagctggtcc atttgatgag     360

ttccagattg ctaccatgct aaaggaaatt ttaaaaggtc tggactatct gcattcagaa     420

aagaaaattc accgagacat aaaagctgcc aatgtcttgc tctcagaaca aggagatgtt     480

aaacttgctg attttggagt tgctggtcag ctgacagata cacagattaa aagaaatacc     540

tttgtgggaa ctccattttg gatggctcct gaagttattc aacagtcagc ttatgactca     600
```

-continued

```
aaagctgaca tttggtcatt gggaattact gctattgaac tagccaaggg agagccacct    660

aactccgata tgcatccaat gagagttctg tttcttattc ccaaaaacaa tcctccaact    720

cttgttggag actttactaa gtcttttaag gagtttattg atgcttgcct gaacaaagat    780

ccatcatttc gtcctacagc aaaagaactt ctgaaacaca aattcattgt aaaaaattca    840

aagaagactt cttatctgac tgaactgata gatcgtttta agagatggaa ggcagaagga    900

cacagtgatg atgaatctga ttccgagggc tctgattcgg aatctaccag cagggaaaac    960

aatactcatc ctgaatggag ctttaccacc gtacgaaaga agcctgatcc aaagaaagta   1020

cagaatgggg cagagcaaga tcttgtgcaa accctgagtt gtttgtctat gataatcaca   1080

cctgcatttg ctgaacttaa acagcaggac gagaataacg ctagcaggaa tcaggcgatt   1140

gaagaactcg agaaaagtat tgctgtggct gaagccgcct gtcccggcat cacagataaa   1200

atggtgaaga aactaattga aaaatttcaa aagtgttcag cagacgaatc cccctaagaa   1260

acttattatt ggcttctgtt tcatatggac ccagagagcc ccaccaaacc tacgtcaaga   1320

ttaacaatgc ttaacccatg agctccatgt gcc                                1353


<210> SEQ ID NO 9
<211> LENGTH: 21
<212> TYPE: DNA
<213> ORGANISM: Artificial Sequence
<220> FEATURE:
<223> OTHER INFORMATION: PCR primer

<400> SEQUENCE: 9

gtctatgata atcacacctg c                                               21


<210> SEQ ID NO 10
<211> LENGTH: 25
<212> TYPE: DNA
<213> ORGANISM: Artificial Sequence
<220> FEATURE:
<223> OTHER INFORMATION: PCR primer

<400> SEQUENCE: 10

ggcacatgga gctcatgggt taagc                                           25


<210> SEQ ID NO 11
<211> LENGTH: 416
<212> TYPE: PRT
<213> ORGANISM: Mus musculus

<400> SEQUENCE: 11

Met Ala His Ser Pro Val Ala Val Gln Val Pro Gly Met Gln Asn Asn
 1               5                  10                  15

Ile Ala Asp Pro Glu Glu Leu Phe Thr Lys Leu Glu Arg Ile Gly Lys
            20                  25                  30

Gly Ser Phe Gly Glu Val Phe Lys Gly Ile Asp Asn Arg Thr Gln Gln
        35                  40                  45

Val Val Ala Ile Lys Ile Ile Asp Leu Glu Glu Ala Glu Asp Glu Ile
    50                  55                  60

Glu Asp Ile Gln Gln Glu Ile Thr Val Leu Ser Gln Cys Asp Ser Ser
65                  70                  75                  80

Tyr Val Thr Lys Tyr Tyr Gly Ser Tyr Leu Lys Gly Ser Lys Leu Trp
                85                  90                  95

Ile Ile Met Glu Tyr Leu Gly Gly Gly Ser Ala Leu Asp Leu Leu Arg
            100                 105                 110
```

-continued

```
Ala Gly Pro Phe Asp Glu Phe Gln Ile Ala Thr Met Leu Lys Glu Ile
        115                 120                 125

Leu Lys Gly Leu Asp Tyr Leu His Ser Glu Lys Lys Ile His Arg Asp
    130                 135                 140

Ile Lys Ala Ala Asn Val Leu Leu Ser Glu Gln Gly Asp Val Lys Leu
145                 150                 155                 160

Ala Asp Phe Gly Val Ala Gly Gln Leu Thr Asp Thr Gln Ile Lys Arg
                165                 170                 175

Asn Thr Phe Val Gly Thr Pro Phe Trp Met Ala Pro Glu Val Ile Gln
            180                 185                 190

Gln Ser Ala Tyr Asp Ser Lys Ala Asp Ile Trp Ser Leu Gly Ile Thr
        195                 200                 205

Ala Ile Glu Leu Ala Lys Gly Glu Pro Pro Asn Ser Asp Met His Pro
    210                 215                 220

Met Arg Val Leu Phe Leu Ile Pro Lys Asn Asn Pro Pro Thr Leu Ile
225                 230                 235                 240

Gly Asp Phe Thr Lys Ser Phe Lys Glu Phe Ile Asp Ala Cys Leu Asn
                245                 250                 255

Lys Asp Pro Ser Phe Arg Pro Thr Ala Lys Glu Leu Leu Lys His Lys
            260                 265                 270

Phe Ile Val Lys Asn Ser Lys Lys Thr Ser Tyr Leu Thr Glu Leu Ile
        275                 280                 285

Asp Arg Phe Lys Arg Trp Lys Ala Glu Gly His Ser Asp Glu Glu Ser
    290                 295                 300

Asp Ser Glu Gly Ser Asp Ser Glu Ser Ser Ser Arg Glu Ser Asn Pro
305                 310                 315                 320

His Pro Glu Trp Ser Phe Thr Thr Val Arg Lys Lys Pro Asp Pro Lys
                325                 330                 335

Lys Leu Gln Asn Gly Glu Glu Gln Asp Leu Val Gln Thr Leu Ser Cys
            340                 345                 350

Leu Ser Met Ile Ile Thr Pro Ala Phe Ala Glu Leu Lys Gln Gln Asp
        355                 360                 365

Glu Asn Asn Ala Ser Arg Asn Gln Ala Ile Glu Glu Leu Glu Lys Ser
    370                 375                 380

Ile Ala Val Ala Glu Thr Ala Cys Pro Gly Ile Thr Asp Lys Met Val
385                 390                 395                 400

Lys Lys Leu Ile Glu Lys Phe Gln Lys Cys Ser Ala Asp Glu Ser Pro
                405                 410                 415
```

<210> SEQ ID NO 12
<211> LENGTH: 2028
<212> TYPE: DNA
<213> ORGANISM: Mus musculus

<400> SEQUENCE: 12

```
aggcaccgcc acaggtcaag ccctgcattc aggaaagaga gcaacactgc agttagccaa      60

aagccaggca ggcgagcggc agagaggcct cgatcgagaa gcctggtaga gctgcagaga     120

tacctccgta ggaggagcca gtctctgccg gaggcgccac cgccaccacc gcagaagcag     180

cgcgaagtag cagtcgccac catggcccac tcaccggtgg ctgttcaagt gcctgggatg     240

cagaataata tagcagatcc agaagaactg ttcacaaaat tagagcgcat tggaaaaggc     300

tcctttggag aagttttcaa aggaattgat aaccgtactc agcaagtggt tgcaattaaa     360

atcattgacc ttgaggaagc tgaggatgaa atagaagaca tccaacaaga aataactgtt     420
```

-continued ttgagtcagt gcgacagctc atatgtaaca aaatactatg ggtcctattt aaagggttca 480
aaactatgga taataatgga atacctaggt ggaggttcag cattggatct tctgcgtgct 540
ggtccatttg atgagttcca gattgccacc atgctcaagg agattttgaa aggtctggac 600
tatctacatt ctgaaaagaa aatccaccga gacattaaag ctgccaacgt cttgctttca 660
gaacaaggtg atgttaaact ggctgacttt ggagttgctg gccagctgac agatacacaa 720
atcaaaagaa acaccttcgt agggactccg ttttggatgg ctcctgaagt tattcaacag 780
tcagcttatg actctaaagc tgacatatgg tctttgggaa ttactgctat tgaacttgcc 840
aagggagagc ctccgaattc tgacatgcat ccaatgagag ttctgtttct tattccaaaa 900
aacaaccctc caactcttat tggagacttt actaagtctt tcaaggagtt tattgatgct 960
tgcctgaata aagacccgtc atttcgtcct acagctaaag aacttttgaa gcataagttc 1020
atcgtaaaaa attcaaagaa gacttcttat ctgactgaat tgatcgatcg atttaagaga 1080
tggaaggcag aaggccacag tgatgaggaa tctgattccg agggctctga ctcggaatcc 1140
agcagcaggg aaagtaaccc tcaccctgaa tggagtttca ccactgtgcg taagaagcct 1200
gatccaaaga aactgcagaa tggggaagag caagatcttg tgcaaacctt gagctgtttg 1260
tctatgataa tcacacctgc atttgccgaa cttaaacagc aggacgagaa taatgcgagt 1320
cgaaaccagg caattgaaga acttgagaaa agtattgctg tggctgaaac cgcctgtcct 1380
ggcatcacag ataagatggt gaagaaacta atcgaaaaat ttcaaaagtg ttctgcggat 1440
gaatcccctt aagaaatctg ttgtcattac ttttggcttc tgtttcatgt ggaccaggag 1500
aaacccacca aagctatgtc aaccttataa atgcttaact catgagctcc atgtgccttt 1560
tggatctttg ccacattgaa gatttagagg aagctattaa actattttgt gatggtgatt 1620
atcattttgt attttaaaga gattattttg taaggaataa ttttaatact atagttttgc 1680
cggtattgta gtaaatgctg agatacaggt tttttgtttt ttgtttttta attttaggta 1740
ccattatttc ttatgttcat ggaatgaata ctgtttggtt tggaatcttt agttaactgt 1800
atactcataa acatacaggt ctttcaaagt catcctaact attaaatgtt tgtaaatcat 1860
caagcttcaa aaagcattct ttttccccca cacaagtata ttctaaaaat gactatttgt 1920
aatgaggtgg aagtaagtaa taccttctta aaacaagtgt ttttaagaag ctcccggaaa 1980
aaaaaaaaaa aaaaaaaaaa aaaaaaaaaa aaaaaaaaaa aaaaaaaa 2028

<210> SEQ ID NO 13
<211> LENGTH: 36
<212> TYPE: DNA
<213> ORGANISM: Artificial Sequence
<220> FEATURE:
<223> OTHER INFORMATION: PCR primer

<400> SEQUENCE: 13
cagcaagtcg ttgctatccg gatcatagac cttgag 36

<210> SEQ ID NO 14
<211> LENGTH: 36
<212> TYPE: DNA
<213> ORGANISM: Artificial Sequence
<220> FEATURE:
<223> OTHER INFORMATION: PCR primer

<400> SEQUENCE: 14
ctcaaggtct atgatccgga tagcaacgac ttgctg 36

HUMAN SIGNAL TRANSDUCTION SERINE/ THREONINE KINASE

This is a divisional under 37 CFR §1.53b of application Ser. No. 09/340,993 filed on Jun. 25, 1999, U.S. Pat. No. 6,034,228, from which priority under 35 USC §120 is claimed.

Which is a Continuation in Part Application from U.S. Application Ser. No. 09/211,930, filed Dec. 15, 1998, U.S. Pat. No. 5,962,265, which claimed priority under 35 USC § 119(a) from UK Application GB 9726851.0 entitled HUMAN SIGNAL TRANSDUCTION SERINE/ THREONINE KINASE, filed Dec. 19, 1997; the entire disclosures of which are each incorporated by reference.

FIELD OF THE INVENTION

The present invention relates to nucleic acid and amino acid sequences pertaining to a novel human signal transduction serine threonine protein kinase. Molecular sequences are provided for the design and synthesis of entities that modulate biological and/or pharmacological activity of the native biomolecule. The sequences are also provided for employment to identify compounds that modulate biological and/or pharmacological activity of the native biomolecule. Biologically-effective antisense molecules are provided, as well as dominant negative mutant versions of the signal transduction kinase which are suitable for therapeutic use. The invention is also drawn toward the study, prevention, diagnosis, and treatment of pathophysiological disorders mediated by the novel biomolecule.

BACKGROUND OF THE INVENTION

Cellular response mechanisms to stress are fundamentally important to the human immune system. Stress responses represent carefully devised cellular defense mechanisms which were developed at an early point during evolution; evidenced by the fact that biomolecules implicated in stress response exhibit remarkable similarity across the animal kingdom. Welch, W. J., et al., *The Stress Response and the Immune System, Inflamnmation*: Basic Principles and Clinical Correlates, Raven Press, Gallin, J. I., et al., Eds., Second Edition, 41:841 (1992).

Lymphocyte activation, homing, resistance to target cell lysis, tumor antigenicity, regulation of proto-oncogene transcription, and immune surveillance are examples of immunologic functions that appear to be mediated or modulated by stress activated signal transduction molecules. Siegelman, M., et al., *Science*, 231:823 (1986); Kusher, D. I., et al., J. Immunol., 145:2925 (1990); Ullrich, S. J., et al., PNAS, 83:3121 (1986); Colotta, F., et al., Biochem. Biophys. Res. Commun., 168:1013 (1990); Haire, R. N., et al., J. Cell Biol, 106:883 (1988); Born, W., et al., Immunol. T., 11:40 (1990). The number of preactivated and MHC class II-restricted autoreactive T-lymphocytes in peripheral blood of patients with rheumatoid arhritis, for example, dramatically increases relative to the levels in healthy individuals. Similarly, peripheral blood T-lymphocytes from patients with inflammatory arthritis proliferate strongly in the absence of exogenous antigen or mitogen. Welch, W. J., et al., *The Stress Response and the Immune System, Inflammation*: Basic Principles and Clinical Correlates, Raven Press, Gallin, J. I., et al., Eds., Second Edition, Chapter 41, 841 (1992). Moreover, synovitis has been shown to result in the generation of oxygen-derived free radicals that act to perpetuate tissue damage. Blake, D. R., et al., Hypoxic-Reperfusion Injury in the Inflamed Human Joint, Lancet, 2:2889 (1989).

The control of hematopoiesis is a highly regulated process that responds to a number of physiological stimuli in the human body. Differentiation, proliferation, growth arrest, or apoptosis of blood cells depends on the presence of appropriate cytokines and their receptors, as well as the corresponding cellular signal transduction cascades. Hu, Mickey C.-T., et al., Genes & Development, 10:2251(1996). Generation of mature leukocytes, for instance, is a highly regulated process which responds to various environmental and physiological stimuli. Cytokines cause cell proliferation, differentiation or elimination, each of these processes being dependent on the presence of appropriate cytokine receptors and the corresponding signal transduction elements. Moreover, the stimulation of quiescent B- and T-lymphocytes occur via antigen receptors which exhibit remarkable homology to cytokine receptors. Grunicke, Hans H., *Signal Transdiuction Mechanisms in Cancer*, Springer-Verlag (1995). See also, Suchard, S. J., et al., *Mitogen-Activated Protein Kinase Activation During IgG-Dependent Phagocytosis in Human Neutrophils*, J. Immunol., 158:4961 (1997).

Distinct signaling cassettes, each containing a central cascade of kinases, respond to a variety of positive and negative extracellular stimuli, lead to changes in transcription factor activity and posttranslational protein modifications in mammalian cells. Kiefer, F., et al., EMBO, Vol. 5, 24:7013 (1996). One such protein kinase cascade, known as the *mitogen-activated protein kinase* (MAPK) cascade, is activated as an early event in the response of leukocytes to various stimuli. Stimulation of this pathway has been observed during growth factor-induced DNA synthesis, differentiation, secretion, and metabolism. The MAPK pathway has a critical role in the transduction of receptor-generated signals from the membrane to the cytoplasm and nucleus. Graves, J. D., et al., *Protein Serine/Threonine Kinases of the* MAPK Cascade, Annals New York Academy of Sciences, 766:320 (1995). It has been established that sustained activation of the MAPK cascade is not only required, but it is sufficient to trigger the proliferation of some cells and the differentiation of others. Cohen, P., *Dissection of Protein Kinase Cascades That Mediate Cellular Response to Cytokines and Cellular Stress*, Advances in Pharmacology, Academic Press, Hidaka, H., et al., Eds., Vol. 36, 15 (1996); Marshall, C. J., Cell, 80:179 (1995). Several interdependent biochemical pathways are activated following either stimulation of resting T-lymphocytes through the antigen receptor or stimulation of activated T-lymphocytes through the interleukin-2 (IL-2) receptor. Many of the events that occur after the engagement of either of these receptors are qualitatively similar, such as the activation of mitogen-activated protein kinase (MAPK) pathways and preexisting transcription factors, leading to the expression of specific growth-associated genes. *Symmetry of the Activation of Cyclin-dependent Kinaes in Mitogen and Growth Factor-stimulated T Lymphocytes*, Jaime F. Modiano, et al., Annals New York Academy of Sciences, 766:134 (1995).

Recent evidence suggests that cellular response to stress is controlled primarily through events occurring at the plasma membrane, overlapping significantly with those important in initiating mitogenic responses. Exposure of cells to biological, chemical, or physical stress agents evokes a series of events leading to the activation of a wide group of genes including transcription factors as well as other gene products that are also rapidly and highly induced in response to mitogenic stimulation. The mitogen-activated protein kinase (MAPK) pathway has been shown to be essential for the mitogenic reponse in many systems. See, e.g., Qin, Y. et al., J.Cancer Res.Clin.Oncol., 120:519 (1994). Moreover, due to the fact that most oncogenes encode growth factors, growth factor receptors, or elements of the intracellular postreceptor signal-transmission machinery, it is becoming increasingly apparent that growth factor signal transduction pathways are subject to an elaborate network of positive and negative cross-regulatory inputs from other transformation-related pathways. Grunicke, Hans H., *Signal Transduction Mechanisms in Cancer*, Springer-Verlag (1995). The Hierarchical organization of the MAPK cascade makes integral protein kinase members particularly good targets for such "cross-talk". *Protein Serine/Threonine Kinases of the* MAPK Cascade, J. D. Graves, et al., Annals New York Academy of Sciences, 766:320 (1995).

Initial triggers for inflammation include physical and chemical agents, bacterial and viral infections, as well as exposure to antigens, superantigens or allergens, all of which have the potential to generate Reactive Oxygen Species (ROS) and to thereby activate second messenger signal transduction molecules. Storz, G., et al., *Transcriptional Regulators of Oxidative Stress-Inducible Genes in Prokaryotes and Eukaryote*, in: Stress-Inducible Cellular Responses, Feige, U., et al., Eds., Birkhauser Verlag (1996). Reactive oxygen radicals, via damage to many cellular components including DNA, can cause cell death or, if less severe, cell cycle arrest at growth-phase checkpoints. Stress damage not only activates checkpoint controls but also activates protein kinases, including the stress activated protein kinases (SAPKs), c-Raf-1 and ERKs, which are integral components of cytoplasmic signal transduction (MAPK) cascades. Pombo, C. M., et al., EMBO, Vol. 15, 17:4537 (1996); Russo, T., et al., J.Biol. Chem., 270:29386 (1995). Considering, inter alia, that stress has also been implicated in oxidant injury, atherosclerosis, neurogenerative processes, and aging, elucidation of the components of mammalian stress-induced pathways should provide more specific targets that can be exploited therapeutically. N. J. Holbrook, et al., *Stress Inducible Cellular Responses*, 273, U. Feige, et al., Eds., Birkhauser Verlag (1996).

Evidence has demonstrated that mitogen-activated protein kinase (MAPK) and stress activated protein kinase (SAPK) signal transduction pathways are responsible for triggering biological effects across a wide variety of pathophysiological conditions including conditions manifested by dysfunctional leukocytes, T-lymphocytes, acute and chronic inflammatory disease, auto-immune disorders, rheumatoid arthritis, osteoarthritis, transplant rejection, macrophage regulation, endothelial cell regulation, angiogenesis, atherosclerosis, fibroblasts regulation, pathological fibrosis, asthma, allergic response, ARDS, atheroma, osteoarthritis, heart failure, cancer, diabetes, obeisity, cachexia, Alzheimers disease, sepsis, and neurodegeneration. As MAP kinases play a central role in signaling events which mediate cellular response to stress, their inactivation is key to the attenuation of the response. N. J. Holbrook, et al., *Stress-Inducible Cellular Responses*, 273, Feige, U., et al., Eds., Birkhauser Verlag (1996).

Despite major efforts to develop new therapeutic approaches Adult Respiratory Distress Syndrome (ARDS) (acute pulmonary inflammation characterized by the massive generation of Reactive Oxygen Species (ROS) within the lung), for example, remains lethal for about 50% of affected patients. Polla. B.S., et al., *Stress Proteins in Inflammation*, in: *Stress Inducible Cellular Responses*, Feige, U., et al. Eds., Birkhauser Verlag (1996). Moreover, the chronic inflammatory disease, rheumatoid arthritis, for instance, is believed to be mediated by activated T-lymphocytes that infiltrate the synovial membrane and initiate a series of inflammatory processes. Panayi, G. S., et al., *The Importance of the T-Cell in Initiating and Maintaining the Chronic Synovitis of Rheumatoid Arthritis*, Arthritis Rheum, 35:729 (1992). Accumulating evidence also indicates that the autoimmune disease multiple sclerosis (MS) is mediated by autoreactive T-lymphocytes. Stinissen, P., et al., Crit. Rev. Immunol., 17(1):33 (1997). Autoreactive T-lymphocytes have been demonstrated to undergo in vivo activation and clonal expansion in patients with MS. Zhang, J., et al., J. Mol. Med., 74(11):653 (1996). In diabetes mellitus, autoreactive T-lymphocytes systematically destroy pancreatic islet cells such that they prove incapable of producing insulin. Another propelling recent development in the implication of overactive T-cells is the recognition that a particular subset of T-lymphocytes appear to be a major culprit in asthma and other allergic diseases, by responding with undue vigor to apparently harmless invaders (rates of asthma per capita in the developing world have increased dramatically in the last several decades; doubling in the U.S. since 1980). *New Clues to Asthma Therapies*: Vogel, G., Science, 276:1643 (1997).

Recently, much progress has been made in defining the signal transduction pathways mediating the cellular response to stress. Pombo, C. M., et al., for instance, report the cloning and characterization of a human Ste20-like oxidant stress response kinase, SOK- 1.The kinase is positively regulated by phohsphorylation and negatively regulated by its C-terminal non-catalytic region. Reported data suggests SOK-1 transduces signals in response to oxidative and environmental stress. EMBO, Vol. 15, 17:4537 (1996). Moreover, Schinkmann, K., et al., recently reported the cloning and characterization of the human STE-20-like kinase, mst-3. The mst-3 transcript is reported to be ubiquitously expressed. Mst-1 is furthermore reported to be positively regulated by autophosphorylation. J. Biol. Chem., 272(45):28695 (1997).Other stress-activated protein kinase (SAPK), members of the MAPK family, have been shown to be activated in situ by inflammatory stimuli, including tumor-necrosis factor (TNF) and interleukin-1. Kyriakis, J. M., et al., Nature, 369:156 (1994); Dérijard, B., et al., Cell, 76:025 (1994); Sánchez, I., et al., Nature, 372:794 (1994). See also, Kiefer, F., et al., EMBO, Vol. 5, 24:7013 (1996); Creasy, C. L., et al., J. Biol. Chem., 271: No. 35, 21049 (1996)); Creasy, C. L., et al., Gene, 167:303 (1995)); Manser, E., et al., Nature, 367:40 (1994); Hu, Mickey C.-T., et al., Genes & Development, 10:2251(1996); Katz, P., et al., J. Biol. Chem., (1994)); Pombo, C. M., et al., Nature, 377:750 (1995).

Integral members of cellular signaling pathways as targets for therapeutic development, for example, have been the subject to several reviews. See, e.g., Levitzki, A., *Signal-Transduction Therapy: A Novel Approach to Disease Management*, Eur. J. Biochem, 226:1 (1994); Powis G., *The Potentialfor Molecular Oncology to Define New Drug Targets*, in: New Molecular Targets for Cancer Chemotherapy, Workman, P., Kerr D. J., eds., CRC Press, Boca Raton FL (1994). As a result of the efforts of numerous laboratories, an impressive list of remarkably specific inhibitors of kinases, for instance, has become available. See, e.g., Levitzki, A., Tyrphostins: *Tyrosine Kinase Blockers as Novel Antiproliferative Agents and Dissectors of Signal Transduction*, FASEB; 6:3275 (1992); Workman P., et al., *Discovery and Design of Inhibitors of Oncogenic Tyrosine Kinases*, in: *New Approaches in Cancer Pharmacology: Drug Design and Development, Springer*, Berlin 55 (1994).

A novel class of pyridinyl imidazoles, CSAIDS [SKB], for instance, have been developed, that inhibit the production of the cytokines interleukin-1 (IL- 1) and tumor necrosis factor (TNF-α) in monocytes. The drug has been demonstrated to bind specifically to one protein in monocytes, termed CSBP (CSAID-binding protein), which has been isolated, cloned, and sequenced and demonstrated as a MAPK homolog. Lee, J. C., et al., *Differential Effects of the BicyclicItnidazoles on Cytokine Synthesis in Human Monocytes and Endothelial Cells*, Agents Actions, 41: C191 (1994); *A Protein Kinase Involved in the Regulation of Inflammatory Cytokine Biosynthesis*, Nature, 372:739 (1994). Moreover, as demonstrated by the identification of rapamycin as a specific inhibitor of the activation of p70 S6 kinase and the identification of compounds that inhibit the EGF receptor protein kinase very potently and that block the activation of MAP kinase kinase have demonstrated that specific inhibitors of protein kinases can indeed be developed. Alessi, D., et al., *A Specific Inhibitor of the Activation of MAP Kinase Kinase*-1 in vitro and in vivo, J. Biol. Chem., 279:27489 (1995); Fry, D., et al., *A Specific Inhibitor of the Epidermal Growth Factor Receptor Tyrosine Kinase*, Science, 265:806 (1994); Cohen, P., *Dissection of Protein Kinase Cascades That Mediate Cellular Response to Cytokines and Cellular Stress*, Intracellular Signal Transduction, Advances in Pharmacology, Hidaka, H., et al., Eds., Academic Press, 36:17 (1996).

Compounds which are able to modulate the activity of specific signal transduction molecules integral to specific intracellular pathways are expected to have significant potential for the ability to control or attenuate downstream physiological responses. Unfortunately, in spite of the introduction of numerous new drugs during the last three decades, there is a need for new, more efficient and less toxic compounds. Accordingly, the ability to identify such compounds is of paramount importance.

SUMMARY OF THE INVENTION

The present invention is directed to an isolated and purified polynucleotide molecule comprising a nucleic acid sequence which encodes a polypeptide comprising an amino acid sequence having at least about 90% homology to a member selected from the group consisting of: (SEQ ID NO:3, SEQ ID NO:3 positions 24–274, and SEQ ID NO:3 positions 275–416).

The current invention is directed to an antisense molecule comprising an oligomer in the range from about 12 to about 25 nucleotides in length which: (a) is complementary to a region within positions 157–232 or positions 1405–1480 of SEQ ID NO: 1.

The invention is further directed to a method of identifying compounds that modulate a biological and/or pharmacological activity of a signal transduction kinase polypeptide, comprising combining a candidate compound modulator with a polypeptide comprising an amino acid sequence having at least about 90% homology to a member selected from the group consisting of: (SEQ ID NO:3, SEQ ID NO:3 positions 24–274, and SEQ ID NO:3 positions 275–416), and measuring an effect of the candidate compound modulator on the biological and/or pharmacological activity of the polypeptide.

The invention is further directed to a method of modulating a biological and/or pharmacological activity of a signal transduction kinase polypeptide in a cell comprising administering an effective amount of a polynucleotide - or - an effective amount of an antisense molecule to said cell.

DETAILED DESCRIPTION OF THE INVENTION

Unless defined otherwise, all technical and scientific terms used herein have the same meaning as is commonly understood by one of skill in the art to which this invention belongs. All publications and patents referred to herein are incorporated by reference.

Biological activity as used herein in reference to the signal transduction serine threonine protein kinase of the present invention refers to the ability of the biomolecule to transduce cellular signals including but not limited to the ability to bind ATP, to autophosphorylate and/or to phosphorylate a substrate and to the ability to directly or otherwise activate any of the biological molecules including but not limited to NFκB, AP-1, and SRF.

Pharmacological activity as used herein in reference to the signal transduction serine threonine protein kinase of the present invention refers to the ability to mediate any one or more of the physiological conditions including but not limited to cell differentiation, proliferation, oncogenic transformation, macrophage regulation, endothelial cell regulation, fibroblasts regulation, cytoskeletal structure, metastases, cell aggregation, cell motility, cytokinesis, acute and chronic inflammatory disease, auto-immune disorders, allergic response, secretion, apoptosis, neurological disorders, peripheral vascular disease, atherosclerosis, and asthma.

Dominant negative mutant as used herein refers to a nucleic acid coding region sequence which has been changed with regard to at least one position in the sequence, relative to the corresponding wild type native version, preferrably at a position which encodes a changed amino acid residue position at an active site required for biological and/or pharmacological activity in the native peptide. Dominant negative mutant embodiments of the invention, for example, include peptides comprising a sequence as depicted in SEQ ID NO:3, SEQ ID NO:3 positions 24–274, or SEQ ID NO:3 positions 275–416 wherein one or more positions corresponding to SEQ ID NO:3 selected from the group consisting essentially of (position 31 (glycine), 33 (glycine), 36 (glycine), 38 (valine), 51 (alanine), 53 (lysine), 144 (aspartic acid), 149 (asparagine), 162 (aspartic acid), 163 (phenylalanine), 164 (glycine), 182 (threonine), 189 (glutamic acid), and 201 (aspartic acid)) are substituted or deleted. Dominant negative mutants are moreover defined to be included within the scope of the disclosure of the variants section infra.

Biologically effective as used herein in reference to antisense nucleic acid molecules as well as dorminant negative mutant nucleic acid coding regions and dominant negative mutant peptides refers to the ability of these molecules to modulate the biological activity and/or pharmnacological activity of the novel signal transduction protein kinase of the present invention and/or transcription/translation of nucleic acid coding regions of the novel signal transduction protein kinase of the present invention.

As used herein, a functional derivative of a biomolecule disclosed herein is an entity that possesses a functional biological activity and/or pharmacological activity as defined herein that is derived from SEQ ID NO:1 or SEQ ID NO:3, for example, truncated versions, versions having deletions, functional fragments, versions having substitutions, versions having insertions or extended ends, or biologically effective dominant negative mutants as well as biologically effective antisense molecules.

The term modulation is used herein to refer to the capacity to either enhance or inhibit a biological activity and/or pharmacological activity of a signal transduction molecule of the present invention or to the capacity to either enhance or inhibit a functional property of a nucleic acid coding region of the present invention. Modulate physiology as used herein refers to the biophysiological regulation of cells and/or tissue and the treatment of pathophysiological disorders related thereto.

Direct administration as used herein refers to the direct administration of nucleic acid molecules, peptides, or compounds which comprise embodiments and/or functional derivatives (e.g., SEQ ID NO:1, SEQ ID NO:3) of the present invention. Direct administration includes but is not limited to gene therapy.

Purified as used herein refers to molecules, either nucleic acid or amino acid sequences, that are removed from their natural environment and isolated or separated from at least one other component with which they are naturally associated.

Expression vector as used herein refers to nucleic acid vector constructions to direct the transcription of nucleic acid regions in host cells. Expression vectors include but are not limited to plasmids, retroviral vectors, viral and synthetic vectors.

Transformed host cells as used herein refer to cells which harbor nucleic acids or functional derivatives of the present invention.

Signal Transduction via Kinases

A cascade signal transduction mechanism is essentially a conduit for the transmittal of an external stimulus to the cell nucleus in order to trigger a distinct pattern of gene expression in response to the stimulation. The extracellular signal is amplified and transduced by a series of independent sequential covalent modifications, from the plasma membrane to the nucleus, via distinct phosphorylation steps of independently specific cognate cytosolic biomolecules. Protein phosphorylation is now acknowledged as the most important means of acute regulation of protein function, signal transduction, and gene expression in eukaryotic cells. Intracellular biomolecule phosphorylation via specific kinases is responsible for switching of cellular activity from one state to another. It is the major mechanism by which cells respond to extracellular signals such as mitogenic stimulation; biological, chemical, and physical stress, hormones, and growth factors. Protein Phosphorylation, Hardie, D. G., Oxford Press (1993).

The protein kinases are a large family of enzymes. Conserved structural motifs provide clear indications as to how the kinases transfer the γ-phosphate of a purine nucleotide triphosphate to the hydroxyl groups of their protein substrates. There are two main subdivisions within the superfamily: the protein-serine/threonine kinases and the protein-tyrosine kinases. The kinase domains that define protein kinases contain 12 conserved subdomains (I-XII) that fold into a common catalytic core structure, as revealed by the 3-dimensional structures of several enzymes. The central core of the catalytic domain, the region with greatest frequency of highly conserved residues, consists of subdomains VI through IX. The most striking indicator of amino acid specificity is found in subdomain VI, the consensus in this region is a strong indicator of serine/threonine specificity. See, e.g., Hanks, S. K., et al., *The Protein Kinase Family: Conserved Features and Deduced Phylogeny of the Catalytic Domains*, Science, 241:42 (1988); Hanks, S. K., et al., *The Eukaryotic Protein Kinase Superfamily: Kinase (Catalytic) Domain Structure and Classification*, FASEB , Ser. Rev., 9:576 (1995).

Protein kinases which have closely related catalytic domains, and thus define a family, represent products of genes that have undergone relatively recent evolutionary divergence. Clustering appears to be of predictive value in the determination of the properties and function of novel protein kinases. Accordingly, members of a given family tend also to share related functions. This is manifest by similarities in overall structural topology, mode of regulation, and substrate specificity. See, generally, Hardie, D. G, . et al., The Protein Kinase Factsbook, Academic Press, London (1995).

Progress has been made by many labs in defining signaling pathways initiated by mitogenic stimuli. Blenis, J., *Signal Transduction via the MAP Kinases*, PNAS, 90:5889 (1993). The MAP kinase family of enzymes have been implicated as common and essential components of signaling pathways induced by diverse mitogenic stimuli. Once activated, MAP kinases phosphorylate a number of substrates including transcription factors essential for triggering gene expression required for the growth response. Accordingly, the MAP kinases are considered to be potentially valuable pharmacological targets within the growth factor signaling pathways. Hidaka, H., et al., *Intracellular Signal Transduction*, Advances in Pharmacology, Academic Press (1996).

Mitogen-activated protein kinases (MAPKs) and their upstream regulatory kinases comprise functional units that couple upstream input signals to a variety of outputs. MAPK cascades have been remarkably conserved in evolution. The core of these cascades is a three-tiered module consisting of an MAPK-extracellular signal-regulated kinase kinase (an MEKK), an MEK and an MAPK or extracellular signal-regulated kinase (ERK). The defining characteristic of these modules is the MAPK itself. The classical pathway, known as the extracellular signal-regulated kinase pathway (ERK), is activated by mitogens and growth factors. ERK has a regulatory kinase, MAPK kinase or MEK, necessary for activation. This enzyme is in turn regulated by another MAPKK kinase known as Raf. Analogous with the classical MAPK module are two other modules which are activated by cytokines and cellular stresses and which have become known as the stress kinase pathways. The defining MAPKs of these pathways are JNK (SAPK) and P38. JNK is activated by the upstream SEK-1 (MKK4) which is activated by MEKK1 or MLK3 whereas P38 is activated by MKK3 and MKK6.

In yeast the MAPK modules operate in a linear manner linking extracellular signals to functional response, whereas in mammalian cells 'cross-talk' between modules may be obligatory in some cases (eg. IL-2 production by T-lymphocytes). Phosphorylation of transcriptional factors (eg. AP-1, NF-kB, ELK-1, ATF-2) by the terminal MAPKs serve to regulate expression of key inflammatory genes. Differences in the expression of the various kinases between cell types and in response to processes in disease will have major impact on how cells respond to extracellular stimuli under physiological and pathological conditions. It is for these reasons that there is very likely to be selectivity for specific inhibitors of these different kinases for their associated physiological role as well as opportunities for therapeutic intervention.

Phosphorylation of transcriptional factors (eg. AP-1, NF-kB, ELK-1, ATF-2) by the terminal MAPKs serve to regulate expression of key inflammatory genes. Differences in the expression of the various kinases between cell types in response to processes in disease will have major impact on how cells respond to extracellular stimuli under physiological and pathological conditions. This should provide opportunities for therapeutic intervention.

Studies of the budding and fission yeasts, *Saccharomyces cerevisiae* and *Schizosaccharomyces pombe*, have been particularly fruitful in the recognition of protein kinases. Hanks, S. K., et al., *The Eukaryotic Protein Kinase Superfamily*, FASEB Ser. Rev., 9:576 (1995). Signal transduction pathways connecting cell surface receptors with each member of the MAPK superfamily in mammalian cells are remarkably similar to those of the budding yeast *Saccharomyces cerevisiae*, in which genetic studies have shown parallel signaling cascades leading to the activation of at least three distinct MAPK-related kinases. Hu, Mickey C.-T., et al., Genes & Development, 10:2251(1996); See, e.g., Herskowitcz, I., et al., Cell, 80:187 (1995).

A component of the pheromone-response pathway in budding yeast, Ste20, represented the first identified member of a new family of serine/threonine protein kinases. Leberer, E., et al., EMBO, 11:4815 (1992); Ramer, S. W., et al., PNAS, 90:452 (1993). Several mammalian homologs to Ste20have since been identified, including MST1 (Creasy, C. L., et al., J. Biol. Chem., 271: No. 35,21049 (1996)), MST2 (Gene, 167:303 (1995)), HPK1 (Kiefer, F., et al., EMBO, Vol. 5,24:7013 (1996)). Recently, mammalian Ste20-like kinases, including p21-activated protein kinase (PAK1) (Manser, E., et al., Nature, 367:40 (1994)) and germinal center kinase (GC kinase) (Katz, P., et al., J. Biol. Chem., (1994)), have been shown to be capable of activating mammalian MAPK cascades. Pombo, C. M., et al., EMBO, Vol. 15, 17:4537 (1996). See also, U.S. Pat. No. 5,605,825, Human PAK65, issued Feb. 25, 1997. Methods described in U.S. Pat. No. 5,605,825 are herein incorporated herein by reference.

The MAP kinases require activation by a MAPK/ERK activating kinase (MEK). The dual-specificity kinase is capable of phosphorylating both tyrosine and serine/threonine residues in proteins. The proto-oncogene c-Raf-1, for instance, has been shown to encode a protein acting as a MEK kinase and the pathway Raf→MEK→MAPK is now well established as a major signal transduction pathway for growth factors. Activated MAPK undergoes a translocation to the nucleus where it can directly phosphorylate and activate a variety of transcription factors including c-Myc, C/EBPβ, $p62^{TCF}$/Elk-1, ATF-2 and c-Jun. Grunicke, Hans H., *Signal Transduction Mechanisms in Cancer, Springer-Verlag* (1995).

The MAP kinase (MAPK) cascade is critical in mediating several intracellular actions. In one pathway a series of protein-protein interactions is triggered at the plasma membrane that culminate in activation of the GTP-binding protein Ras. GTP-Ras then interacts with the protein kinase Raf, recruiting it to the plasma membrane where it is activated. The activation of Raf is followed by the sequential activation of three additional kinases: MAP kinase kinase (MAPKK), MAPK, and MAPK-activated protein (MAPKAP) kinase-1. The activation of MAPK and MAPKAP kinase-1 leads to their translocation from the cytosol to the nucleus where they regulate the activities of transcription factors. Cohen, P., *Dissection of Protein Kinase Cascades That Mediate Cellular Response to Cytokines and Cellular Stress*, Advances in Pharmacology, Academic Press, Hidaka, H., et al., Eds., Vol. 36, 15 (1996); Marshall, C. J., Cell, 80:179 (1995).

Recent evidence suggests that cellular response to stress is controlled primarily through events occurring at the plasma membrane, overlapping significantly with those important in initiating mitogenic responses. Exposure of cells to stress agents, as mentioned supra, evokes a series of events leading to the activation of a wide group of genes including transcription factors as well as other gene products that are also rapidly and highly induced in response to mitogenic stimulation. Pathways which are involved in mediating these cellular responses rely on the activation of mitogen-activated protein kinases (MAPK) which include extracellular signal-regulated kinases (ERK), stress activated protein kinases (SAPK), c-Jun N-terminal kinases (JNK), and p38/PK/CSBP kinases. These kinases play a key role in the activation of transcription factors and other regulatory proteins involved in activating gene expression. Phosphorylation enhances complex formation and the serum response element located in the promoters of stress response genes such as c-fos. Other regulated proteins include $p90^{RSK}$, activating transcription factor-2 (ATF-2, a cAMP response element-binding protein), NF-IL6 (nuclear factor for the activation of Interleukin 6) and c-Myc. Davis, R. J., *The Mitogen-Activated Protein Kinase Signal Transduction Pathway*, J. Biol. Chem., 268:1553 (1993); N. J. Holbrook, et al., *Stress Inducible Cellular Responses*, 273, in: Stress-Inducible Cellular Responses, Feige, U., et al., Eds., Birkhauser Verlag (I 996). The mitogen-activated protein kinase (MAPK) pathway has been shown to be essential for the mitogenic reponse in many systems. See, e.g., Qin, Y. et al., J. Cancer Res. Clin. Oncol., 120:519 (1994). Moreover, due to the fact that most oncogenes encode growth factors, growth factor receptors, or elements of the intracellular postreceptor signal-transmission machinery, it is becoming increasingly apparent that growth factor signal transduction pathways are subject to an elaborate network of positive and negative cross-regulatory inputs from other transformation-related pathways. Grunicke, Hans H., *Signal Transduction Mechanisms in Cancer*, Springer-Verlag (1995). The Hierarchical organization of the MAPK cascade makes integral protein kinase members particularly good targets for such “cross-talk”. *Protein Serine/Threonine Kinases of the MAPK Cascade*, J. D. Graves, et al., Annals New York Academy of Sciences, 766:320 (1995).

Initial triggers for inflammation include physical and chemical agents, bacterial and viral infections, as well as exposure to antigens, superantigens or allergens, all of which have the potential to generate Reactive Oxygen Species (ROS) and to thereby activate second messenger signal transduction molecules. Reactive oxygen species are generated from molecular oxygen and include the free radicals superoxide ($.O_2^{-}$), hydroxyl (.OH) and nitric oxide (NO.), as well as non-radical intermediates such as hydrogen peroxide ($H_2O_2$) and singlet oxygen ($^1O_2$). During normal cellular respiration, ROS are constantly produced at low rate in both eukaryotes and prokaryotes. At these low concentrations, ROS can act as second messengers, stimulate cell proliferation, and act as mediators for cell activation. However, during phagocytosis, infection or inflammation, ROS can accumulate to toxic levels which leads to oxidative stress, and may damage almost all cellular components. All organisms have mechanisms to detoxify the oxidants or to repair the damage caused by ROS, including superoxide dismutases, catalases, peroxidases, glutathione, thioredoxin, and heat shock proteins. The expression of the genes coding these proteins (oxidative stress genes) is induced by changes in the concentrations of ROS, suggesting that cells have developed mechanisms to sense the ROS. Storz, G., et al., *Transcriptional Regulators of Oxidative Stress-Inducible Genes in Prokaryotes and Eukaryote*, in: Stress-Inducible Cellular Responses, Feige, U., et al., Eds., Birkhauser Verlag (1996).

SOK-1

Pombo et al. recently reported the cloning and characterization of human Ste20/oxidant stress response kinase, SOK-1 which belongs to the Sps1/GC kinase group of Ste20-like kinases with N-terminal catalytic domains. The kinase is positively regulated by phohsphorylation and negatively regulated by its C-terminal non-catalytic region. SOK-1 is activated relativcly specifically by oxidant stress. Reported data places SOK-1 in a stress response pathway and suggest it resembles in function yeast Ste20s which transduce signals in response to environmental stress. EMBO, Vol. 15, 17:4537 (1996). The open reading frame is reported to encode a protein of 426 amino acids and has a predicted $M_r$ of 48,041 Da. The kinase domain is located in the N-terminal half of the protein. The reported peptide contains all 11 subdomains of serine/threonine kinases. Ste20 related stress-activated kinases are evidenced to be in proximity to the membrane in the signaling cascade and therefore are able to provide greater target opportunity for selective modulation of signal transduction.

MST-3

Schinkmann et al. recently reported the cloning and characterization of the human STE-20-like kinase, mst-3. The mst-3 transcript is reported to be ubiquitously expressed, is most closely related to SOK-1, and is furthermore reported to be positively regulated by autophosphorylation. A cDNA molecule composed of 1976 bases has been described as well as an open reading frame which encodes a 431 amino acid peptide (SEQ ID NO:5) having a molecular mass of 48kDa. The mst-3 kinase is reported to consist of an N-terminal kinase domain and a 142-amino acid C-terminal regulatory domain. The mst-3 molecule shares 68.8% overall amino acid homology with SOK-1. J. Biol. Chem., 272(45):28695 (1997).

Novel Human Signal Transduction Serine/Threonine Kinase

A novel human signal transduction serine/threonine protein kinase molecule, as well as example nucleic acid sequences which encode therefor, are herein described.

A cDNA sequence is provided, SEQ ID NO:1, which comprises the structural coding region of the native human signal transduction kinase, SEQ ID NO:2. The 3201 bp SEQ ID NO:1 contiguous cDNA sequence contains a 1251 bp open reading frame (ORF) with a Kozak initiation sequence at the start methionine. SEQ ID NO:2 shows the 1251 base open reading frame including the stop codon. The native human homolog of the Ste20-like signal transduction kinase is shown in SEQ ID NO:3. The 416 amino acid residue sequence of the novel protein contains all eleven (11) sudomains found in eukaryotic protein kinases including Ste20-like kinases. SEQ ID NO:3 has 65.7 and 71 percent homology to the Ste20/oxidant stress response kinse-1 (SOK-1), SEQ ID NO:4, described by Pombo et al., and to the mammalian Ste20-like kinase (MST-3), SEQ ID NO:5, described by Schinkmann et al., respectively. EMBO, Vol. 15, 17:4537 (1996); J. Biol. Chem., 272(45):28695 (1997). The novel kinase has a predicted molecular weight of 46527.83 daltons, an isoelectric point of 5.097, and a net charge of −13 at pH 7.0.

Mitogen-activated protein kinase cascades have been remarkably conserved in evolution. SEQ ID NO:4, for example, shows the 426 amino acid residue sequence of SOK-1 which is the recently described human MAPK-pathway oxidant: (stress) activated kinase. SOK-1 has been characterized as a human homolog of the MAPK-pathway yeast stress-activated kinase Ste20. Pombo, C. M., et al., EMBO, Vol. 15, 17:4537 (:1996). Pombo et al. reported SEQ ID NO:4 as a human Ste20/oxidant stress response kinase. Ste20 related stress-activated kinases, via evidentiary characterization, appear to be close to the plasma membrane in the signaling cascade and therefore may have significant potential to provide greater target opportunity for selective modulation of signal transduction. EMBO, Vol. 15, 17:4537 (1996).

Some features of the cDNA SEQ ID NO:1 are for instance: bases 1–181 represent the 5' UTR, bases 176–185 represent the Kozak sequence, bases 182–1432 represent CDS, bases 1433–3201 represent 3' UTR, bases 3194–3199 represent the poly adenylation signal.

Some features of the 416 residue polypeptide (SEQ ID NO:3) are for instance: Molecular Weight 46527.83 Daltons, 51 Strongly Basic(+) Amino Acids (K,R), 65 Strongly Acidic(−) Amino Acids (D,E), 138 Hydrophobic Amino Acids (A,I,L,F,W,V), 103 Polar Amino Acids (N,C,Q,S,T, Y), Isolectric Point=5.097, Charge at PH 7.0=−13.017.

Eukaryotic protein kinases each contain a conserved catalytic domain region of 250–300 amino acid residues which is responsible for the phosphotransferase activity of the enzyme. The catalytic domain of the novel signal transduction kinase described herein (SEQ ID NO:3) has 89 and 87.5 percent similarity, respectively, with the catalytic domain of mst-3 (SEQ ID NO:5) and SOK-1 (SEQ ID NO:4). Catalytic domains can be further divided into 12 subdomains defined by strings of invariant and conserved residues. Residue positions 31–38 of the novel signal transduction kinase, for instance, correspond to the consensus kinase subdomain I GxGxxGxV. Subdomain II is involved in the phosphotransfer reaction and identified by an invariant lysine in the tripeptide sequence AxK. With regard to the novel kinase SEQ ID NO:3, subdomain II is found in residues 51–53 (AIK). Subdomains VI through IX, characterized by a large number of highly conserved residues, form the central core of catalytic activity. SEQ ID NO:3 comprises the invariant or nearly invariant residues $Asp^{144}$ and $Asn^{149}$ in subdomain VI and $Asp^{162}$, $Phe^{163}$, and $Gly^{1164}$ in subdomain VII; all of which have been implicated in ATP binding. Region VIB contains the consensus sequence HRDLxxxN, with D being the invariant $Asp^{144}$. SEQ ID NO:3 in this region is HRDIKAAN (wherein the substitution of Ile for Leu is conservative). Moreover, the novel signal transduction kinase contains the conserved DFG of subdomain VII. The Asp functions to orient the γ-phosphate of the ATP for transfer. Subdomain VIII of SEQ ID NO:3 contains the highly conserved APE sequence, with the Glu corresponding to the invariant $Glu^{189}$. This subdomain is thought to play a critical role in the recognition of substrate binding. Additionally, many kinases are known to be activated by phosphorylation of residues in subdomain VIII. The sequence DxWS/AxG of subdomain IX is represented by amino acid positions 201–206 of SEQ ID NO:3 (DIWSLG). This region forms a large α-helix and the initial Asp of the consensus sequence serves to stabilize the catalytic loop by hydrogen bonding.

SEQ ID NO:3 is capable of autophosphorylation and substrate phosphorylation (e.g., myelin basic protein). SEQ ID NO:3 positions 24–274 represent the catalytic domain of the serine threonine signal transduction kinase. SEQ ID NO:3 positions 275–416 represent the regulatory region. Therefore, particularly preferred embodiments of the current invention are polynucleotides which comprise a nucleic acid sequence which encodes a polypeptide comprising an amino acid sequence of SEQ ID NO:3 positions 24–274, or SEQ ID NO:3 positions 275–416. Polypeptides are preferred which comprise SEQ ID NO:3 amino acid positions 24–274 and/or SEQ ID NO:3 positions 275–416.

Expression in Immune Tissues

Northern blot analysis identifies a primary transcript pertaining to the novel signal transduction kinase of approximately 3.5 kb in length. Prominent transcripts are apparent primarily in immune tissues (expressed at a particularly high level in tissues of the human immune system, i.e., lymph node, peripheral blood leukocytes, spleen, fetal liver, bone marrow, thymus, and placenta) as well as from placenta and cancer-cell lines. See, EXAMPLE V. Expression of the novel kinase appears to be in sharp contrast to the mst-3 transcript which is reported to be ubiquitously expressed. J. Biol. Chem., 272(45):28695 (1997).

Activation of Transcription Factors by TEN-1 Kinase

The signal transduction kinase (SEQ ID NO:3) is demonstrated herein to activate NFκB, AP1, and SRF when overexpressed in cell lines (e.g., HEK293, HeLa). In addition, expression of an antisense CDNA has been shown to inhibit both basal and TNFa-mediated activation of NFκB in ECV304 cells. Shown in Example XI is the general format of the transcription activation reporter assays used to determine if SEQ ID NO:3 activates specific transfactors. The PathDetect™ System (including reporter constructs and positive control constructs) was used to perform these assays. Stratagene, La Jolla, Calif. All assays were performed in triplicate and repeated several separate times.

The signal transduction kinase (SEQ ID NO:3) activates NFκB, AP1, and SRF when overexpressed in HEK293 and HeLa cells. In addition, SEQ ID NO:1 anti-sense cDNA expression in ECV304 cells is capable of inhibiting both basal and TNFa stimulated inductions of NFκB by approximately 66% and 50%, respectively. SEQ ID NO:3 is able to activate transcription factors (e.g. NFκB, AP1) in vivo that are known to initiate transcription of numerous inflammatory genes including pro-inflammatory cytokines, chemokines, inflammatory enzymes, adhesion molecules, and inflammatory receptors. In addition, NFκB synergistically interacts with AP1 to promote gene transcription. The co-operativity between NFκB and other transcription factors activated by inflammatory signals underlie the specificity of the inflammatory response in many different diseases.

NFκB, AP1, and SRF are activated in 293 cells by the signal transduction kinase SEQ ID NO:3. MEKK is a known activator of NFκB and is supplied as part of the Stratagene PathDetect™ System. Moreover, AP-1, and SRF are activated in HeLa cells by the signal transduction kinase SEQ ID NO:3. MEKK is a known activator of AP1 and is supplied as part of the Stratagene PathDetect™ System. PKA (protein kinase A) is a known activator of SRF and is supplied as part of the Stratagene PathDetect™ System. SEQ ID NO:1 antisense molecules greatly reduce the basal level and TNF α-mediated NFκB activation in ECV304 cells.

Example Dominant Negative Mutants

A preferred polynucleotide of the present invention comprises a nucleic acid sequence which encodes a polypeptide comprising the sequence as depicted in SEQ ID NO:3 wherein one or more positions of SEQ ID NO:3 selected from the group consisting essentially of (position 31 (glycine), 33 (glycine), 36 (glycine), 38 (valine), 51 (alanine), 53 (lysine), 144 (aspartic acid), 149 (asparagine), 162 (aspartic acid), 163 (phenylalanine), 164 (glycine), 182 (threonine), 189 (glutamic acid), and 201 (aspartic acid)) are substituted or deleted. See, for instance, Example X.

Variants

The present invention relates to nucleic acid (e.g., SEQ ID NO:1 and SEQ ID NO:2) and amino acid sequences (e. (g., SEQ ID NO:3) of the novel human signal transduction kinase and variations thereof as well as functional derivatives and to the use of these sequences to identify compounds that modulate the biological and/or pharmacological activity of the signal transduction molecule. Further, the invention relates to biologically effective antisense nucleic acid molecules as well as nucleic acids which encode biologically effective dominant negative mutant versions of the signal transduction kinase as well as biologically effective dominant negative mutant versions of the novel peptide biomolecule. The present invention also provides a method of treatment for a patient in need of such treatment, videlicet for a patient who suffers a pathological condition mediated by the SEQ ID NO:3 signal transduction kinase, comprising administering an effective amount of a biologically effective antisense nucleic acid molecule derived from SEQ ID NO:1; or administering an effective amount of a nucleic acid which encodes a biologically effective dominant negative mutant version of the signal transduction kinase; or administering a compound that modulates the biological and/or pharmacological activity of SEQ ID NO:3 which was identified by a method described herein.

The present invention also encompasses variants of the human signal-transduction kinase molecule SEQ ID NO:3. A preferred variant, for instance, is a polypeptide comprising a fragment having at least 90% amino acid sequence homology (identity) to SEQ ID NO:3; a more preferred variant is one having at least 93% amino acid sequence homology; and a most preferred variant is one having at least 95% amino acid sequence homology to the signal-transduction kinase amino acid sequence as depicted in SEQ ID NO:3 or a biologically and/or pharmacologically active substantial fragment thereof, e.g., SEQ ID NO:3 positions 24–274, and SEQ ID NO:3 positions 275–416. Variants within the scope of this invention also include dominant negative mutants of these contemplated embodiments, examples of which are set forth herein.

A variant of the SEQ ID NO:3 signal-transduction kinase molecule of the present invention may have an amino acid sequence that is different by one or more amino acid substitutions. Embodiments which comprise amino acid deletions and/or additions are also contemplated. The variant may have conservative changes (amino acid similarity), wherein a substituted amino acid has similar structural or chemical properties, for example, the replacement of leucine with isoleucine. A variant may have nonconservative changes, e.g., replacement of a glycine with a tryptophan. Embodiments within the intended scope of the invention also include SEQ ID NO:3 having one or more amino acid deletions or insertions, or both. Guidance in determining which and how many amino acid residues may be substituted, inserted or deleted without abolishing biological or proposed pharmacological activity may be reasonably inferred in view of this disclosure and may be further be found using computer programs well known in the art, for example, DNAStar software. *Amino acid substitutions of SEQ ID NO:*3 may be made, for instance, on the basis of similarity in polarity, charge, solubility, hydrophobicity, hydrophilicity, and/or the amphipathic nature of the residues as long as a biological and/or pharmacological activity of the native molecule is retained. However, amino acid substitutions are important to construct contemplated *biologically effective dominant negative mutants*, several species of which are set forth herein.

Negatively charged amino acids, for example, include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine. However, in the construction of biologically effective dominant negative mutants at least one amino acid residue position at an active site required for biological and/or pharmacological activity in the native peptide is changed to produce an agent or entity having reduced activity or which is devoid of detectable native wild type activity.

Suitable substitutions of amino acids include the use of a chemically derivatized residue in place of a non-derivatized residue. D-isomers as well as other known derivatives may also be substituted for the naturally occurring amino acids. See, e.g., U.S. Pat. No. 5,652,369, *Amino Acid Derivatives*, issued Jul. 29, 1997. Example substitutions are set forth in TABLE 1 as follows:

TABLE 1

| Original residue | Example conservative substitutions |
|---|---|
| Ala (A) | Gly; Ser; Val; Leu; Ile; Pro |
| Arg (R) | Lys; His; Gln; Asn |
| Asn (N) | Gln; His; Lys; Arg |
| Asp (D) | Glu |
| Cys (C) | Ser |
| Gln (Q) | Asn |
| Glu (E) | Asp |
| Gly (G) | Ala; Pro |
| His (H) | Asn; Gln; Arg; Lys |
| Ile (I) | Leu; Val; Met; Ala; Phe |
| Leu (L) | Ile; Val; Met; Ala; Phe |
| Lys (K) | Arg; Gln; His; Asn |
| Met (M) | Leu; Tyr; Ile; Phe |
| Phe (F) | Met; Leu; Tyr; Val; Ile; Ala |
| Pro (P) | Ala; Gly |
| Ser (S) | Thr |
| Thr (T) | Ser |
| Trp (W) | Tyr; Phe |
| Tyr (Y) | Trp; Phe; Thr; Ser |
| Val (V) | Ile; Leu; Met; Phe; Ala |

"Homology" is a measure of the identity of nucleotide sequences or amino acid sequences. In order to characterize the homology, subject sequences arc aligned so that the highest order homology (match) is obtained. "Identity" per se has an art-recognized meaning and can be calculated using published techniques. Computer program methods to determine identity between two sequences, for example, include DNAStar software (DNAStar Inc., Madison, Wis.); the GCG program package (Devereux, J., et al., Nucleic Acids Research (1984) 12(1):387); BLASTP, BLASTN, FASTA (Atschul, S.F. et al., J Molec Biol (1990) 215:403). Homology (identity) as defined herein is determined conventionally using the well known computer program, BESTFIT (Wisconsin Sequence Analysis Package, Version 8 for Unix, Genetics Computer Group. University Research Park, 575 Science Drive, Madison, Wis. 53711). When using BESTFIT or any other sequence alignment program to determine whether a particular sequence is, for example, about 90% homologous to a reference sequence, according to the present invention, the parameters are set such that the percentage of identity is calculated over the full length of the reference nucleotide sequence or amino acid sequence and that gaps in homology of up to about 10% of the total number of nucleotides in the reference sequence are allowed. Ninety percent of homology is therefore determined, for example, using the BESTFIT program with parameters set such that the percentage of identity is calculated over the full length of the reference sequence, e.g., SEQ ID NO:3, and gaps of up to 10% of the total number of amino acids in the reference sequence are allowed, and wherein up to 10% of the amino acid residues in the reference sequence may be deleted or substituted with another amino acid, or a number of amino acids up to 10% of the total amino acid residues in the reference sequence may be inserted into the reference sequence. Percent homologies are likewise determined, for example, to identify preferred species, within the scope of the claims appended hereto, which reside within the range of about 90 percent to 100 percent homology to SEQ ID NO:3 as well as biologically and/or pharmacologically active functional derivatives thereof and biologically effective dominant negative mutants contemplated herein.

Percentage similarity (conservative substitutions) between two polypeptides may also be scored by comparing the amino acid sequences of the two polypeptides by using programs well known in the art, including the BESTFIT program, by employing default settings for determining similarity.

The present invention relates to nucleic acid sequences and amino acid sequences of the signal-transduction kinase and variants thereof and to the use of these sequences to identify compounds that modulate the biological and/or pharmacological activity of a signal transduction molecule.

Polynucleotide sequences which encode the signal-transduction kinase as depicted in SEQ ID NO:3 and variants thereof contemplated herein are particularly preferred embodiment of the present invention. *Biologically effective* antisense molecules and nucleic acids which encode biologically effective dominant negative mutant versions of SEQ ID NO:3, or derivatives thereof, as well as dominant negative mutant versions of SEQ ID NO:3, and derivatives thereof, examples of each of which are described infra, are preferred embodiments of the present invention and are intended to fall within the scope of the claims appended hereto.

The present invention relates to nucleic acid sequences (e.g., SEQ ID NO:1 and SEQ ID NO:2) and amino acid sequences (e.g., SEQ ID NO:3, SEQ ID NO:3 positions 1–86, SEQ ID NO:3 positions 87–124, SEQ ID NO:3 positions 125–155, SEQ ID NO:3 positions 248–266, SEQ ID NO:3 positions 266–288, and SEQ ID NO:3 positions 289–298) of the novel human signal transduction kinase as well as inherent derivatives thereof, e.g., functional derivative that demonstrate or perform substantially the same biological and/or pharmacological activity in substantially the same way. The invention is also intended to encompass biologically and/or pharmacologically active truncated versions clearly derived from the sequences disclosed and characterized herein (e.g., evidenced domains described infra) as well as chimeric sequences which contain one or more of them.

The nucleic acid sequence also provides for the design of antisense molecules, examples of which are provided, which are useful in downregulating, diminishing, or eliminating expression of the genomic nucleotide sequence in cells including leukocytes, endothelial cells, and tumor or cancer cells.

The human signal-transduction kinase molecule of the present invention can also be used in screening assays to identify antagonists or inhibitors which bind, emulate substrate, or otherwise inactivate or compete with the biomolecule. The novel kinase can also be used in screening assays to identify agonists which induce the production of or prolong the lifespan of the molecule in vivo or in vitro.

The invention also relates to pharmaceutical compounds and compositions comprising the kinase molecule substantially as depicted in SEQ ID NO:3, or fragments thereof, antisense molecules capable of disrupting expression of the naturally occurring gene, and agonists, antibodies, antagonists or inhibitors of the native signal-transduction kinase.

These compositions are useful for the prevention or treatment of conditions associated with abnormal expression of the signal transduction molecule such as described infra.

Pharmacological Significance

Compounds which are able to modulate the activity of specific signal transduction molecules integral to specific intracellular pathways are expected to have significant potential for the ability to control or attenuate downstream physiological responses. Significant evidence has been provided that stress kinase activation pathways are responsible for biological effects across a wide variety of disease areas. As MAP kinases play a central role in signaling events which mediate cellular response to stress; compounds which modulate or inactivate specific integral signal transduction molecules, i.e., the novel human stress-activated serine/threonine signal transduction kinase molecule described herein, SEQ ID NO:3, and nucleic acid sequences coding therefor, e.g. SEQ ID NO:1 and SEQ ID NO:2, have significant potential for the ability attenuate pathophysiological responses. Accordingly, the ability to screen for antagonists and agonists which modulate the activity of the native human stress-activated serine/threonine signal transduction kinase molecule described herein is significantly valuable toward the identification and development of therapeutic agents.

Potential diagnostic and therapeutic applications are readily apparent for modulators of the human Ste20-like signal transduction serine/threonine kinase described herein. Areas which are common to disease particularly in need of therapeutic intervention include but are not limited to pathophysiological disorders manifested by dysfunctional leukocytes, T-cell activation, acute and chronic inflammatory disease, auto-immune disorders, rheumatoid arthritis, osteoarthritis, transplant rejection, macrophage regulation, endothelial cell regulation, angiogenesis, atherosclerosis, fibroblasts regulation, pathological fibrosis, asthma, allergic response, ARDS, atheroma, osteoarthritis, heart failure, cancer, diabetes, obeisity, cachexia, Alzheimers, sepsis, neurodegeneration, and related disorders.

Oxidants, mechanical stress, UV irradiation, and immunologic mediators lead to the activation of proinflammatory gene products, apoptosis-related genes, and acute phase response genes. These responses are the underlying causes of vascular injury and inflammation. In view of the recent literature, it is generally accepted that MAPK pathways including the SAPK/JNK and p38 kinase pathways, for example, are central components in the response of cells to chemical, mechanical and proinflammatory assaults. With such a prominent role in cell activation, stress kinases are likely to play an important role in disease areas including, but not limited to, stroke (ischemia reperfusion), ARDS, sepsis, neurodegeneration, and inflammation. During reperfusion of ischemic tissue, for instance, there is a marked increase in stress activated protein kinase activity leading to c-Jun/ATF-2 activation to enhance gene transcription leading to either apoptosis or differentiation and cell repair. In the inflammatory response, TNF-α and IL-1β activate p38, which triggers production of more TNF and IL-1, which amplifies the inflammatory response. This process is thought to play a role in both septic shock and formation of the athersclerotic plaque. SAPKs are also thought to play a role in the induction of E-selectin expression in endothelial cells and matrix metalloproteinases in inflammatory cells, indicating a role for SAPKs in postischemic injury and tissue remodeling. Moreover, SAPK-p46β$_1$, a brain-specific kinase, colocalizes with the prominent Alzheimer's disease marker, ALZ-50, suggesting that the proline-directed hyperphosphorylation of tau protein is catalyzed by this kinase.

The signal-transduction kinase homolog described herein (SEQ ID NO:3) is believed to transduce cellular response to stressors leading to the activation of proinflammatory gene products. The deleterious effects of the mediators of inflammation, including ROS and cytokines, open new avenues for the development of original anti-inflammatory therapies. As MAP kinases play a central role in signaling events which mediate cellular response to stress, their inactivation or antagonization is key to the attenuation of the response. Clear evidence has been shown, for instance, that ERK and JNK pathways are strongly linked to IL-2 production. ERK and JNK pathways are clearly established to be required for full T-lymphocyte activation leading to IL-2 gene transcription and T-cell proliferation. Interruption of the signaling process by selective kinase inhibition is therefore expected to reduce IL-2 production and T-lymphocyte proliferation which would be therapeutically beneficial in chronic inflammatory diseases. MAPKs including stress activated kinases are expected to play key roles in the pathology of autoimmune diseases including but not limited to rheumatoid arthritis (RA), osteoarthritis (OA), and multiple sclerosis (MS). Accordingly, the novel human serine/threonine stress-activated kinase signal transduction molecule described herein (SEQ ID NO:3), and nucleic acid sequences coding therefor, e.g. SEQ ID NO:1 and SEQ ID NO:2, have significant potential as a specific targets that can be exploited diagnostically and therapeutically for the control of dysfunctional leukocytes, including but not limited to dysfunctional T-lymphocytes, and in the treatment of autoimmune disease including rheumatoid arthritis (RA) and osteoarthritis (OA), and in the study, diagnosis, and treatment of acute and chronic inflammation including but not limited to conditions such as asthma and ARDS as well as other diseases manifested by dysfunctional leukocytes.

Excess production of oxidants is responsible for the activation of MAPK pathways. Excess production of oxidants is also common to the major atherosclerotic risk factors as well as to ischaemic reperfusion injury. Lipid peroxidation in cell membranes, cytoplasmic free radicals, together with 'oxidative stress' lead to activation of AP-1 and NF-kB. The JNK pathway has been established as well as activation of Ras appears to be involved in the responses. Stimulation of macrophages and endothelial cells by LPS or TNF/IL-1 results in the activation of MAPK, JNK and P38 pathways. The selective P38 inhibitor SB203580, for example, has been clearly shown to inhibit production of TNF and IL-1 by LPS- stimulated macrophages as well as TNF, IL-6 and IL-8 by TNF-stimulated HUVECs. Philip Cohen, *Dissection of Protein Kinase Cascades That Mediate Cellular Response to Cytokines and Cellular Stress*, in: Intracellualr Signal Transduction, Advances in Pharmacology, Vol. 36, Academic Press (1996). MAPK pathways are also activated by shear stress. Atherosclerotic lesions develop and progress in areas of low and unstable shear stress and not in areas exposed to steady shear. Acute changes in shear stress activate MAPK pathways and chronic stress desensitizes MAPK and NF-kB pathways indicating that these pathways are activated.

Transient shear stress can activate inflammatory genes partly through activation of the JNK pathway and AP-1 although the ERK pathway is also activated. Despite major efforts to develop new therapeutic approaches Adult Respiratory Distress Syndrome (ARDS) (acute pulmonary inflammation characterized by the massive generation of Reactive Oxygen Species (ROS) within the lung) remains lethal for about 50% of affected patients. Polla. B. S., et al., *Stress Proteins in Inflammation*, in: *Stress Inducible Cellular*

*Responses*, Feige, U., et al. Eds., Birkhauser Verlag (1996). Accordingly, the novel human serine/threonine stress-activated kinase signal transduction molecule described herein (SEQ ID NO:3), and nucleic acid sequences coding therefor, e.g., SEQ ID NO:1 and SEQ ID NO:2, have significant potential as specific targets that can be exploited diagnostically and therapeutically for the control of patho-physiologies relating to inflammation, dysfunctional macrophages, dysfunctional endothelial cells, and related inflammatory diseases including but not limited to conditions such as atherosclerosis, asthma, allergic response, ARDS, heart failure, Atheroma and related disorders.

Differentiation, proliferation, growth arrest, or apoptosis of cells depends on the presence of appropriate cytokines and their receptors, as well as the corresponding cellular signal transduction cascades. It remains clear that stress kinase pathways, make critical contributions to transformation. In view of the positioning of raf-MEK1-Erk11/2downstream of ras, the antiproliferative biological effect of inhibiting signal transduction in the MAP kinase pathway have significant therapeutic potential, applicable, for example, but not limited to tumours harbouring oncogenic ras. Moreover, activation of stress pathway kinases has been implicated in mediating apoptosis by agents such as TNF in model systems. Evidence regarding the involvement of intracellular signalling pathways in the maintenance of cellular survival suggests that survival and mitogenic signals can be separable and that the balance between these signals plays a key role in determining the fate of transformed cells. There are also indications that perturbation of this balance provides selective apoptosis. It would be critical to achieve optimum selectivity between pathways to achieve apoptosis promotion in tumour cells.

Unfortunately, in spite of the introduction of numerous new drugs during the last three decades, only very modest progress can be registered with regard to both cure or survival rates of cancer patients treated with anti-tumor agents. Thus, there is a need for new, more efficient and less toxic compounds. The majority of presently used anti-tumor agents interfere with the biosynthesis of nucleic acids or their intracellular function. Compounds which inhibit uncontrolled growth by interfering with mitogenic signal transduction may act as cytostatic rather than cytotoxic drugs. Furthermore, attenuation of cellular proliferation has frequently been shown to cause tissue differentiation. Finally, blockade of mitogenic stimulation in a cell can result in the induction of apoptosis or programmed cell death. Accordingly, the novel human serine/threonine stress-activated kinase signal transduction molecule described herein (SEQ ID NO:3), and nucleic acid sequences coding therefor, e.g. SEQ ID NO:1 and SEQ ID NO:2, have significant potential as a specific targets that can be exploited diagnostically and therapeutically to control cancer and the proliferation of tumor cells.

Activation of members of each of the MAPK pathways has been demonstrated in response to endothelin, serum, PDGF and TGFβ in various types of 'fibroblast'. Dominant negatives of ERK1 and Rac have been demonstrated, for example, to inhibit expression of a collagen promotor/reporter gene in TGFβ-stimulated 3T3 fibroblasts. Moreover, in stellate liver cells, for instance, evidence has been shown that Raf and the JNK pathway interact to control cell proliferation and collagen expression. A number of cytokines, some of which are known to activate SAPKs in cells, have been implicated in cachexia. Accordingly, the novel human serine/threonine stress-activated kinase signal transduction molecule described herein (SEQ ID NO:3), and nucleic acid sequences coding therefor, e.g. SEQ ID NO:1 and SEQ ID NO:2, have significant potential as specific targets that can be exploited diagnostically and therapeutically in the control of dysfunctional fibroblasts, including but not limited to conditions such as pathological fibrosis, and cachexia as well as other diseases manifested by dysfunctional fibroblasts.

The establishment and remodeling of blood vessels is controlled by paracrine signals, many of which are protein ligands that bind and modulate the activity of transmembrane receptor tyrosine kinases (RTKs). The basic view of RTK signaling has come from studies (performed largely in fibroblasts) of ligand-dependent autophosphorylation and activation of the branched Ras pathways. The results suggest that most RTKs are similarly coupled into the intracellular signal transduction cascade and are capable of inducing cell proliferation. Hanahan, D., *Signaling Vascular Morphogenesis and Maintenance, Science*, 227:48 (1997). Angiogenic response of vascular endothelium, endothelial cell proliferation, is one of the first steps in the angiogenic process which has clearly been demonstrated to be induced by hypoxia stress. VEGF, bFGF, and EGF all have been demonstrated to upregulate MAPK in HUVEC cells. Accordingly, the novel human serine/threonine stress-activated kinase signal transduction molecule described herein (SEQ ID NO:3), and nucleic acid sequences coding therefor, e.g. SEQ ID NO:1 and SEQ ID NO:2, have significant potential as specific targets that can be exploited diagnostically and therapeutically to control angiogenesis as well as other manifestations of dysfunctional fibroblasts.

Stress-activated protein kinase (SAPK), members of the ERK family, are activated in situ by inflammatory stimuli, including tumour-necrosis factor (TNF). TNF is believed to be responsible for the development of insulin resistance associated with obesity. Exposure of cultured cells to TNFα induces insulin resistance which is believed to be mediated by the Type I TNFα receptor and intracellular signalling mechanisms. In view of the evidence that TNFα is intimately associated with the activation of Stress Activated Protein Kinases (SAPKs), the novel human serine/threonine stress-activated kinase signal transduction molecule described herein (SEQ ID NO:3), and nucleic acid sequences coding therefor, e.g. SEQ ID NO:1 and SEQ ID NO:2, have significant potential as specific targets that can be exploited diagnostically and therapeutically to control Diabetes and related disorders.

The leptin receptor belongs to the cytokine receptor superfamily of which several members have been shown to feed into SAPK pathways. Intracellular signalling pathways utilised by leptin and the potential for regulation of the leptin receptor through "cross-talk" with other signalling pathways is expected to lead to the design of novel therapeutic approaches for the treatment of obesity. Accordingly, the novel human serine/threonine stress-activated kinase signal transduction molecule described herein (SEQ ID NO:3), and nucleic acid sequences coding therefor, e.g. SEQ ID NO:1 and SEQ ID NO:2, have significant potential as specific targets that can be exploited diagnostically and therapeutically to control Obesity and related disorders.

Compounds which modulate or inactivate specific signal transduction molecules integral to specific cytosolic pathways generally have significant potential for the ability to modulate or attenuate downstream physiological responses. Accordingly, the ability to screen for compounds which modulate the activity of the native human stress-activated serine/threonine signal transduction kinase molecule described herein is of paramount importance toward the development of therapeutic agents.

Functional Constructions

The cDNA for the kinase of the present invention has been subcloned into several expression vectors as examples of providing recombinant protein useful for drug screen assays and/or for employment in vivo or otherwise of the physiological role of the kinase. Expression studies are performed using either constitutive, induced, or tissue specific expression systems in mammalian cell lines. The constructs herein described are example embodiments to be used to transfect mammalian cell lines, e.g., U937 and other well-known cell lines, in order to provide recombinant protein suitable for use in drug screen assays. Constructs are contemplated for over-expressing the wild-type and/or dominant negative kinase of the present invention for characterization its physiological role including activation stimuli, identification of signal transduction pathways, identification of protein-protein interactions, as well as validation of optimal drug candiates.

The nucleic acid sequences which encode the novel kinase can be subcloned into an expression vector in the antisense orientation to provide a tool for producing gene knock-out studies of gene function. Down-regulation of the native signal transduction kinase molecule described herein is also contemplated using antisense expression.

SEQ ID NO:6 and SEQ ID NO:7 are oligonucleotide PCR primers used to produce full-length nucleic acid sequence amplicon pertaining to the novel human stress activated kinase. A shuttle construct containing a nucleic acid coding region of the novel signal transduction kinase was produced by "TA" cloning of the PCR amplicon (SEQ ID NO:8), described infra, into the pCR2.1 vector (Invitrogen, Carlsbad, Calif.).

A GST-Kinase fusion expression vector, designed to express a N-terminal Glutathione S-transferase fusion protein (produced using pGEX5×1, Pharmacia Biotech, Inc., Piscataway, New Jersey), was constructed by subcloning the signal transduction kinase cDNA from the pCR2.1 vector into the pGEX5×1 vector. The signal transduction kinase cDNA was excised from the pCR2.1 vector by restriction digestion using EcoRI and EcoICRI. The fragment was gel purified, then inserted into pGEX5×1 which had been digested with EcoRI and SmaI restriction endonucleases and gel purified. Insertion of the signal transduction kinase cDNA into pGEX5×1 yielded a chimeric EcoICRI:SmaI site which was no longer recognizable by either restriction enzyme. The ligated DNA was used to transform DH5α competent *E. coli* cells (Life Technologies, Gaithersburg, MD). Single, isolated transformed *E. coli* colonies were grown in selective media (LB broth, carbenicillin) overnight at 37° C. and subsequently used to prepare plasmid DNA (Qiagen Plasmid DNA preparation kit). Clones were sequenced (ABI PRISM™ Dye Terminator Cycle sequencing on ABI PRISM™ 377 automated sequencer) to identify correctly inserted cDNA. A correctly cloned construct was selected and used to transform BL21 competent *E. coli cells (Novagen, Inc.) for expression. Expression and purification of the GST/human kinase fusion protein is described infra in EXAMPLE IX.*

Kinase Activity

A kinase activity assay was used to demonstrate the novel signal transduction kinase SEQ ID NO:3 is a functional kinase. Recombinant GST-SEQ ID NO:3 was expressed in BL21 (DE3) *E. coli* cells and purified as outlined in Example IX. The recombinant kinase was tested for catalytic activity as shown in Example II. GST in place of GST-SEQ ID NO:3 kinase shows no phosphorylation and indicates that phosphorylation in the presence of SEQ ID NO:3 is due to its kinase activity and not due to a co-purified contaminant.

To construct a $His_6$-Xpress epitope tagged novel human signal transduction kinase mammalian expression vector the novel kinase protein coding region was excised from the pCR2.1 construct using EcoRI (5') and EcoICRI (3') and inserted into the pcDNA3.1HisC vector (Invitrogen) at the EcoRI (5') and EcoRV (3') sites. Joining of the EcoICRI site from the pCR2.1 contruct to the EcoRV site from the pcDNA3.1HisC vector results in the loss of both sites due to a blunt ended ligation. The resulting construct encodes an epitope tagged kinase protein containing 6 histidine residues and the "Xpress" antibody epitope at the N-terminus of the novel kinase protein. Expression of the epitope tagged novel signal transduction kinase in eukaryotic cells is effected by tansfecting mammalian cell lines either transiently or stably with expression vectors containing the novel kinase coding region. The transformed cells serve as sources of kinase for screening candidate compound modulators, inter alia.

Generally Acceptable Vectors

In accordance with the present invention, polynucleotide sequences which encode the novel kinase, fragments of the polypeptide, fusion proteins or functional equivalents thereof may be used in recombinant DNA molecules that direct the expression of the signal transduction molecule in appropriate host cells. Due to the inherent degeneracy of the genetic code, other DNA sequences which encode substantially the same or a functionally equivalent amino acid sequence, may be used to clone and express the novel human signal-transduction kinase. As will be understood by those of skill in the art, it may be advantageous to produce novel kinase-encoding nucleotide sequences possessing non-naturally occurring codons.

Specific initiation signals may also be required for efficient translation of a signal-transduction kinase sequence. These signals include the ATG initiation codon and adjacent sequences. In cases where the novel kinase, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic.

Cloned signal transduction kinase cDNA obtained through the methods described herein may be recombinantly expressed by molecular cloning into an expression vector containing a suitable promoter and other appropriate transcription regulatory elements, and transferred into prokaryotic or eukaryotic host cells to produce the kinase polypeptide. Techniques for such manipulations are fully described in Sambrook, J., et al., Molecular Cloning Second Edition, Cold Spring Harbor Press (1990), and are well known in the art.

Expression vectors are described herein as DNA sequences for the transcription of cloned copies of genes and the translation of their mRNAs in an appropriate host cell. Such vectors can be used to express nucleic acid sequences in a variety of hosts such as bacteria, bluegreen algae, plant cells, insect cells, fungal cells, human, and animal cells. Specifically designed vectors allow the shuttling of DNA between hosts such as bacteria-yeast, or bacteria-animal cells, or bacteria-fungal cells, or bacteria-invertebrate cells.

A variety of mammalian expression vectors may be used to express the recombinant human kinase molecule disclosed herein in mammalian cells. Commercially available mammalian expression vectors which are suitable for recombinant expression, include but are not limited to, pcDNA3 (Invitrogen), pMClneo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and IZD35 (ATCC 37565), pLXIN and pSIR (CLONTECH), pIRES-EGFP (CLONTECH). INVITROGEN corporation provides a wide variety of commercially available mammalian expression vector/systems which can be effectively used with the present invention. INVITROGEN, Carlsbad, Calif. See, also, PHARMINGEN products, vectors and systems, San Diego, Calif.

Baculoviral expression systems may also be used with the present invention to produce high yields of biologically active protein. Vectors such as the CLONETECH, BacPak™ Baculovirus expression system and protocols are preferred which are commercially available. CLONTECH, Palo Alto, Calif. Miller, L. K., et al., Curr. Op. Genet. Dev. 3:97 (1993); O'Reilly, D. R., et al., *Baculovirus Expression Vectors: A Laboratory Manual*, 127. Vectors such as the INVITROGEN, MaxBac™ Baculovirus expression system, insect cells, and protocols are also preferred which are commercially available. INVITROGEN, Carlsbad, Calif.

Example Host Cells

Host cells transformed with a nucleotide sequence which encodes the human kinase of the present invention may be cultured under conditions suitable for the expression and recovery of the encoded protein from cell culture. Particularly preferred embodiments of the present invention are host cells transformed with a purified polynucleotide comprising a nucleic acid sequence encoding the polypeptide having the sequence substantially as depicted in SEQ ID NO:3 or a biologically active fragment thereof. Cells of this type or preparations made from them may be used to screen for pharmacologically active modulators of the novel human signal-transduction kinase activity.

Eukaryotic recombinant host cells are especially preferred. Examples include but are not limited to yeast, mammalian cells including but not limited to cell lines of human, bovine, porcine, monkey and rodent origin, and insect cells including but not limited to Drosophila and silkworm derived cell lines. Cell lines derived from mammalian species which may be suitable and which are commercially available, include but are not limited to, L cells L-M(TK−) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616),BS-C-1 (ATCC CCL 26) and MRC-5 (ATCC CCL 171).

The expression vector may be introduced into host cells expressing the novel kinase via any one of a number of techniques including but not limited to transformation, transfection, lipofection, protoplast fusion, and electroporation. Commercially available kits applicable for use with the present invention for hererologous expression, including well-characterized vectors, transfection reagents and conditions, and cell culture materials are well-established and readily available. CLONTECH, Palo Alto, Calif.; INVITROGEN, Carlsbad, Calif; PHARMINGEN, San Diego, Calif.; STRATAGENE, LaJolla, Calif. The expression vector-containing cells are clonally propagated and individually analyzed to determine the level of novel kinase protein production. Identification of host cell clones which express the novel kinase may be performed by several means, including but not limited to immunological reactivity with antibodies described herein, and/or the presence of host cell-associated specific kinase activity, and/or the ability to covalently cross-link specific substrate to the novel kinase with the bifunctional cross-linking reagent disuccinimidyl suberate or similar cross-linking reagents.

The signal transduction molecule of the present invention may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals (Porath, J., Protein Exp. Purif. 3:263 (1992)), protein A domains that allow purification on immobilized immunoglobulin, and the domain utilized in the FLAGS extension/affinity purification system (Immunex Corp, Seattle Was.). The inclusion of a cleavable linker sequences such as Factor XA or enterokinase (Invitrogen, San Diego Calif.) between the purification domain and TMP is useful to facilitate purification.

Systems such as the CLONTECH, TALON™ nondenaturing protein purification kit for purifying 6xHis-tagged proteins under native conditions and protocols are preferred which are commercially available. CLONTECH, Palo Alto, Calif.

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phospholylation, lipidation and acylation. Post-translational processing which cleaves a nascent form of the protein may also be important for correct insertion, folding and/or function. Different host cells such as CHO, HeLa, MDCK, 293,WI38,NIH-3T3, HEK293 etc., have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express the novel kiriase may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

The human kinase can be produced in the yeast S. cerevisiae following the insertion of the optimal cDNA cistron into expression vectors designed to direct the intracellular or extracellular expression of the heterologous protein. In the case of intracellular expression, vectors such as EmBLyex4 or the like are ligated to the beta subunit cistron. See, e.g., Rinas, U., et al., Biotechnology, 8:543 (1990); Horowitz, B., et al., J. Biol. Chem., 265:4189 (1989). For extracellular expression, the kinase cistron is ligated into yeast expression vectors which may employ any of a series of well-characterized secretion signals. The levels of expressed novel kinase are determined by the assays described herein.

A variety of protocols for detecting and measuring the expression of the novel kinase, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes may be employed. Well known competitive binding techniques may also be employed. See, e.g., Hampton, R., et al. (1990), *Serological Metlhods—a Laboratory Manual*, APS Press, St Paul Minn.; Maddox, D. E., et al., J. Exp. Med. 158:1211.

Screening Assays

The present invention is also directed to methods for screening for compounds which modulate the expression of DNA or RNA encoding the novel kinase polypeptide, as well as the function of the signal-transduction kinase polypeptide in vivo. Compounds that modulate the expression of DNA or RNA encoding the signal-transduction kinase polypeptide or the function of the polypeptide may be detected by a variety of assays. The assay may be a simple "yes/no" assay to determine whether there is a change in expression or function. The assay may be made quantitative by comparing the expression or function of a test sample with the levels of expression or function in a standard sample.

The signal-transduction kinase described herein, its immunogenic fragments or oligopeptides can be used for screening therapeutic compounds in any of a variety of drug screening techniques. The fragment employed in such a test may be free in solution, affixed to a solid support, borne on a cell surface, or located intracellularly. The abolition of activity or the formation of binding complexes, between the signal-transduction kinase polypeptide and the agent being tested, may be measured. Accordingly, the present invention provides a method for screening a plurality of compounds for specific binding affinity with the signal-transduction kinase polypeptide or a fragment thereof, comprising providing a plurality of compounds; combining the signal-transduction kinase polypeptide of the present invention or a fragment thereof with each of a plurality of compounds for a time sufficient to allow binding under suitable conditions; and detecting binding of the kinase polypeptide, or fragment thereof, to each of the plurality of compounds, thereby identifying the compounds which specifically bind the signal-transduction kinase polypeptide.

Methods of identifying compounds that modulate the activity of a signal-transduction kinase polypeptide are generally preferred, which comprise combining a candidate compound modulator of a signal-transduction kinase activity with a polypeptide of a signal-transduction kinase having the sequence substantially as depicted in SEQ ID NO:3,and measuring an effect of the candidate compound modulator on the kinase activity. Polypeptides which comprise the human signal-transduction kinase, SEQ ID NO:3,its functional fragments or oligopeptides including but not limited to SEQ ID NO:3 positions 24–274,and SEQ ID NO:3 positions 275–416,as well as variants contemplated herein can be used for screening prospective therapeutic compounds in any of a variety of drug screening techniques.

Methods of identifying compounds that modulate a biological and/or pharmacological activity of a signal transduction kinase polypeptide are generally preferred which comprise combining a candidate compound modulator with a purified polypeptide comprising the amino acid sequence as depicted in SEQ ID NO:3 or a variant of SEQ ID NO:3 having at least about 90% homology to a member selected from the group consisting essentially of: (SEQ ID NO:3, SEQ ID NO:3 positions 24–274,and SEQ ID NO:3 positions 275–416) and measuring an effect of the candidate compound modulator on the biological and/or pharmacological activity of the polypeptide. See, Examples.

A further method of identifying compounds that modulate a biological and/or pharmacological activity of a polypeptide comprising the amino acid sequence as depicted in SEQ ID NO:3 or a variant of SEQ ID NO:3 having at least about 90% homology to a member selected from the group consisting essentially of: (SEQ ID NO:3,SEQ ID NO:3 positions 24–274, and SEQ ID NO:3 positions 275–416) comprises combining a candidate compound modulator with a host-cell which expresses the signal transduction kinase polypeptide, and measuring an effect of the candidate compound modulator on the biological and/or pharmacological activity of the polypeptide.

A filter assay based on the protocol of Reuter et al. (1995) is also used to screen for compounds which modulate the activity of the novel kinase described herein: Starting with MBP coated 96-well FlashPlates® (NEN™ Life Science Products) reaction buffer (3X kinase reaction buffer (KRB) contains: 60 mM HEPES (pH 7.5), 30 mM magnesium acetate, 0.15 mM ATP, 3 mM DTT, 0.03 mM sodium orthovanadate) is added, 0.25$\mu$Ci [$\gamma^{33}$P]-ATP at a concentration no greater than 1 $\mu$g/ml, (determined by titration of individual enzyme preparations for a concentration that allows kinetic determinations over a 1 hour time course of the human kinase) of the human kinase are added to each well and incubated 1 hour at 30° C. in the presence or absence of 10 $\mu$M test compound. Total reaction volume is 100 $\mu$L. The reaction is stopped by the addition of EDTA (pH 7.0) to a final concentration of 80 mM. The samples are centrifuged and 50 $\mu$L of the supernatant spotted on p81 cation-exchange filter paper (Whatman, No. 3698 915). The filters are then washed 3 times in 200 mL of 180 mM $H_3PO_4$ (5–10 min each), and once in 200 mL of 96% ethanol. After air drying the filters, radioactivity is determined by Cerenkov counting in a scintillation counter. Compounds which inhibit kinase activity≧50 percent at 10 $\mu$M are indicated by a>50% reduction in scintillation counts. Specificity and selectivity studies is determined by titration of inhibitory compounds to determine the $IC_{50}$ (or other standard quantitation well known in the art for comparison) and by the substitution of other kinases in the assay. For example, determination of relative inhibitory activity of the kinase in comparison to recombinant SOK-1 and/or mst-3, expressed and isolated in a similar manner, assayed under similar conditions, provides selectivity data. Reuter, C. W. M., Catling, A. D. and Weber, M. J., *Immune Complex Kinase Assays for Mitogen-Activated Pirotein Kinase and MEK*, Methods In Enzymology, 255:245 (1995).

See EXAMPLES VI and VII.

To evaluate the ability of a candidate agent to inhibit human tumor growth, human tumor cells are injected into SCID mice (severe combined immunodeficiency) to form palpable tumor masses. The effects of an candidate agent in inhibiting tumor growth can be determined as follows. Approximately $1\times10^7$ cells of the CCL 221 cell line (ATCC, Rockville, Md.), a human ras-dependent colon adenocarcinoma cell line, is suspended in 100 $\mu$l DMEM and injected subcutaneously into SCID mice, such that two tumors per mouse are formed. SCID mice receive CCL 221 cells and the tumors are grown for 7 days without treatment; on the 7th day (Day 0) tumor maximal diameters and animal weights are recorded and the mean tumor size for the mice is determined. On Day 1 (eight days following tumor cell injection), treatment of the mice with candidate agent or vehicle alone is begun. One group of the mice (controls) are injected intraperitoneally with 0.2 ml of vehicle and a second group of mice received agent by intraperitoneal injection. Various doses of agent can be tested in separate groups of mice. On Day 7 and Day 14, animal weight and maximal tumor diameter is measured. Average maximal tumor size for each group on Day 0, Day 7, and Day 14 are compared Day 14, one high dose animal was followed for an additional to determine whether the agent produces a dose-dependent inhibition of tumor growth. Toxicity effects can be examined by tracking mice weight and by harvesting lungs, livers, and spleens of the animals for histological staining.

Compounds which are identified generally according to methods described, contemplated, and referenced herein that modulate the biological and/or pharmacological activity of a signal-transduction molecule of the sequence substantially as depicted in SEQ ID NO:3 are especially preferred embodiments of the present invention.

A method of modulating a biological and/or pharmacological activity of a signal transduction kinase in a cell, tissue, or organism is preferred which comprises administering an effective amount of a polynucleotide contemplated herein. 'Polynucteotide' includes a polynucleotide comprising a nucleic acid sequence which encodes a polypeptide comprising an amino acid sequence having at least about 90% homology to SEQ ID NO:3, SEQ ID NO:3 positions 24–274, and SEQ ID NO:3 positions 275–416; as well as a polynucleotide comprising a nucleic acid sequence which encodes a polypeptide comprising an amino acid sequence wherein one or more positions corresponding to SEQ ID NO:3, selected from the group consisting of (position 31 (glycine), 33 (glycine), 36 (glycine), 38 (valine), 51 (alanine), 53 (lysine), 144 (aspartic acid), 149 (asparagine), 162 (aspartic acid), 163 (phenylalanine), 164 (glycine), 182 (threonine), 189 (glutamic acid), and 201 (aspartic acid)), are substituted or deleted; as well as antisense molecules which are complementary to a region within SEQ ID NO:1 positions 157–232 or 1405–1480, example therapeutic embodiments of which are set forth supra.

An especially preferred embodiment of the present invention is a method for treatment of a patient in need of such treatment for a condition which is mediated by the human signal-transduction kinase described herein comprising administration of a therapeutically effective amount of a human signal-transduction kinase modulating compound.

Yeast 2-Hybrid System

In another embodiment of the invention, a nucleic acid sequence which encodes a human signal-transduction kinase molecule substantially as depicted in SEQ ID NO:3 or a biologically active fragment thereof may be ligated to a heterologous sequence to encode a fusion protein. For example, for screening compounds for modulation of biological activity, it may be useful to encode a chimeric kinase molecule as described herein for expression in hererologous host cells. Chimeric constructs may also be used to express a 'bait', according to methods well known using a yeast two-hybrid system, to identify accessory native peptides that may be associated with the novel human signal-transduction kinase molecule described herein. Fields, S., et al., Trends Genet., 10:286 (1994); Allen, J. B., et al., TIBS, 20:511 (1995). A yeast two-hybrid system has been described wherein protein:protein interactions can be detected using a yeast-based genetic assay via reconstitution of transcriptional activators. Fields, S., Song, O., Nature 340:245 (1989). The two-hybrid system used the ability of a pair of interacting proteins to bring a transcription activation domain into close proximity with a DNA-binding site that regulates the expression of an adjacent reporter gene. Commercially available systems such as the CLONTECH, Matchmaker™ systems and protocols may be used with the present invention. CLONTECH I, Palo Alto, Calif. See also, Mendelsohn, A. R., Brent, R., Curr. Op. Biotech., 5:482 (1994); Phizicky. E. M., Fields, S., Microbiological Rev., 59(1):94 (1995); Yang, M., et al., Nucleic Acids Res., 23(7):1152 (1995); Fields, S., Sternglanz, R., TIG, 10(8) :286 (1994); and U.S. Pat. No. 5,283,173, *System to Detect Protein-Protein Interactions*, and 5,468,614, which are incorporated herein by reference.

Purification via Affinity Columns

It is readily apparent to those skilled in the art that methods for producing antibodies may be utilized to produce antibodies specific for the human kinase polypeptide fragments, or the full-length nascent human kinase polypeptide. Specifically, it is readily apparent to those skilled in the art that antibodies may be generated which are specific for the fully functional receptor or fragments thereof.

Kinase polypeptide antibody affinity columns are made by adding the antibodies to Affigel-10 (Biorad), a gel support which is activated with N hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) with appropriate detergent and the cell culture supernatants or cell extracts containing human signal-transduction kinase polypeptide made using appropriate membrane solubilizing detergents are slowly passed through the column. The column is then washed with phosphate buffered saline/detergent until the optical density falls to background, then the protein is eluted with 0.23M glycine-HCl (pH 2.6)/detergent. The purified human signal-transduction kinase polypeptide is then dialyzed against phosphate buffered saline/detergent.

Recombinant kinase molecules can be separated from other cellular proteins by use of an immunoaffinity column made with monoclonal or polyclonal antibodies specific for full length nascent human kinase polypeptide, or polypeptide fragments of the kinase molecule.

Human kinase polypeptides described herein may be used to affinity purify biological effectors from native biological materials, e.g. disease tissue. Affinity chromatography techniques are well known to those skilled in the art. A human signal-transduction kinase peptide described herein or an effective fragment thereof, is fixed to a solid matrix, e.g. CNBr activated Sepharose according to the protocol of the supplier (Pharmacia, Piscataway, N.J.), and a homogenized/buffered cellular solution containing a potential molecule of interest is passed through the column. After washing, the column retains only the biological effector which is subsequently eluted, e.g., using 0.5M acetic acid or a NaCl gradient.

Antisense Molecules

Various nucleic acid sequences complementary to SEQ ID NO:1 and/or SEQ ID NO:2 provided herein may be used in another embodiment of the invention to modulate the expression of a serine threonine kinase or a biological function of a downstream signal transduction molecule or transcriptional activator, by affecting the transcription and/or translation of sequences corresponding to SEQ ID NO:1 and/or SEQ ID NO:2 in cells. Pharmacological activity of the endogenous gene may be modulated by affecting the transcription and/or translation, for example, of the endogenous gene by use or administration of anti-sense constructs to produce anti-sense transcripts or by direct delivery of anti-sense oligomers. Antisense constructs and oligomers may each be used as embodiments of the present invention and each are related to therapeutic method embodiments practiced via direct administration as defined herein. Example species are provided.

Antisense molecules which comprise oligomers in the range from about 12 to about 25 nucleotides which are complementary to regions of SEQ ID NO:1 and/or SEQ ID NO:2 are preferred embodiments of the invention. Antisense molecules comprising oligomers from about 12 to about 25 nucleotides in length which are complementary to a region within the SEQ ID NO:I positions 157–232 or 1405–1480 are particularly preferred embodiments. Oligonucleotides which comprise sequences complementary to the following positions of SEQ ID NO:1 are therefore example embodiments of the invention:

SEQ ID NO:1 positions 157–232 in progressive increments of twelve (twelve-mers), illustrated as follows: positions 157–168, 158–169, 159–170, 160–171, . . . et seq (all inclusive) . . . 219–230, 220–231, 221–232. This demonstrates 65 example embodiments.

SEQ ID NO:1 positions 1405–1480 in progressive increments of twelve (twelve-mers), illustrated as follows: positions 1405–1416, 1406–1417, 1407–1418, 1408–1419, . . . et seq (all inclusive) . . . 1467–1478, 1468–1479, 1469–1480. This demonstrates another 65 example embodiments.

Oligonucleotides which comprise sequences complementary to and hybridizable to each of the recited areas of the human serine threonine kinase mRNA are contemplated for therapeutic use. Moreover, U.S. Pat. No. 5,639,595*, Identification of Novel Drugs and Reagents*, issued Jun. 17, 1997, wherein methods of identifying oligonucleotide sequences that display in vivo activity are thoroughly described, is herein incorporated by reference.

Nucleotide sequences that are complementary to the serine threonine kinase encoding nucleic acid sequence can be synthesized for antisense therapy. These antisense molecules may be DNA, stable derivatives of DNA such as phosphorothioates or methylphosphonates, RNA, stable derivatives of RNA such as 2'-O-alkylRNA, or other oligonucleotide mimetics. U.S. Pat. No. 5,652,355*, Hybrid Oligonucleotide Phosphorothioates*, issued Jul. 29, 1997, and U.S. Pat. No. 5,652,356*, Inverted Chimeric and Hybrid Oligonucleotides*, issued Jul. 29, 1997, which describe the synthesis and effect of physiologically-stable antisense molecules, are incorporated by reference. Serine threonine kinase antisense molecules may be introduced into cells by microinjection, liposome encapsulation or by expression from vectors harboring the antisense sequence. Antisense therapy may be particularly useful for the treatment of diseases where it is beneficial to modulate the effective biological and/or pharmacological activity of the serine threonine kinase presented herein.

Gene Therapy

A human signal-transduction kinase polypeptide described herein may administered to a subject via gene therapy. Moreover, a polypeptide of the present invention may be delivered to the cells of target organs in this manner. Conversely, signal-transduction kinase polypeptide antisense gene therapy may be used to reduce the expression of the polypeptide in the cells of target organs. The human signal-transduction kinase polypeptide coding region can be ligated into viral vectors which mediate transfer of the kinase polypeptide DNA by infection of recipient host cells. Suitable viral vectors include retrovirus, adenovirus, adeno-associated virus, herpes virus, vaccinia virus, polio virus and the like. See, e.g., U.S. Pat. No. 5,624,820*, Episomal Expression Vector for Human Gene Therapy*, issued Apr. 29, 1997. Nucleic acid coding regions of the present invention are incorporated into effective eukaryotic expression vectors, which are directly administered or introduced into somatic cells for gene therapy (a nucleic acid fragment comprising a coding region, preferably mRNA transcripts, may also be administered directly or introduced into somatic cells). See, e.g., U.S. Pat. No. 5,589,466, issued Dec. 31, 1996. Such nucleic acids and vectors may remain episomal or may be incorporated into the host chromosomal DNA as a provirus or portion thereof that includes the gene fusion and appropriate eukaryotic transcription and translation signals, i.e, an effectively positioned RNA polymerase promoter 5' to the transcriptional start site and ATG translation initiation codon of the gene fusion as well as termination codon(s) and transcript polyadenylation signals effectively positioned 3' to the coding region. Alternatively, the human signal-transduction kinase polypeptide DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo, as well as in vivo human signal-transduction kinase polypeptide gene therapy according to established methods in this art.

Compositions

Pharmaceutically useful compositions comprising the novel human kinase polypeptide DNA, human kinase polypeptide RNA, antisense sequences, or the human kinase polypeptide, or variants and analogs which have the human kinase activity or otherwise modulate its activity, may be formulated according to known methods such as by the admixture of a pharmaceutically acceptable carrier. Examples of such carriers and methods of formulation may be found in *Remington's Pharmaceutical Sciences* (Maack Publishing Co, Easton, Pa.). To form a pharmaceutically acceptable composition suitable for effective administration, such compositions will contain an effective amount of the protein, DNA, RNA, or modulator.

Therapeutic or diagnostic compositions of the invention are administered to an individual in amounts sufficient to treat or diagnose human signal-transduction kinase polypeptide related disorders. The effective amount may vary according to a variety of factors such as the individual's condition, weight, sex and age. Other factors include the mode of administration.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as *Remington's Pharmaceutical Sciences.*

Pharmaceutical compositions suitable for use in the present invention include compositions wherein the active ingredients are contained in an effective amount to achieve the intended purpose. The determination of an effective dose is well within the capability of those skilled in the art. The therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans. A therapeutically effective dose refers to that amount of protein or its antibodies, antagonists, or inhibitors which ameliorate the symptoms or condition. The exact dosage is chosen by the individual physician in view of the patient to be treated.

Compounds identified according to the methods disclosed herein may be used alone at appropriate dosages defined by routine testing in order to obtain optimal modulation of a signal-transduction kinase, or its activity while minimizing any potential toxicity. In addition, co-administration or sequential administration of other agents may be desirable.

The pharmaceutical compositions may be provided to the individual by a variety of routes such as subcutaneous, topical, oral and intramuscular. Administration of pharmaceutical compositions is accomplished orally or parenterally. Methods of parenteral delivery include topical, intra-arterial (directly to the tissue), intramuscular, subcutaneous, intramedullary, intrathecal, intraventricular, intravenous, intraperitoneal, or intranasal administration. The present invention also has the objective of providing suitable topical, oral, systemic and parenteral pharmaceutical formulations for use in the novel methods of treatment of the present invention. The compositions containing compounds identified according to this invention as the active ingredient for use in the modulation of signal-transduction kinase can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a signal-transduction kinase modulating agent.

The daily dosage of the products may be varied over a wide range from 0.01 to 1,000 mg per adult human/per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. Even more particularly, the range varies from about 0.05 to about 1 mg/kg. Of course the dosage level will vary depending upon the potency of the particular compound. Certain compounds will be more potent than others. In addition, the dosage level will vary depending upon the bioavailability of the compound. The more bioavailable and potent the compound, the less compound will need to be administered through any delivery route, including but not limited to oral delivery. The dosages of the human signal-transduction kinase modulators are adjusted when combined to achieve desired effects. On the other hand, dosages of these various agents may be independently optimized and combined to achieve a synergistic result wherein the pathology is reduced more than it would be if either agent were used alone. Those skilled in the art will employ different formulations for nucleotides than for proteins or their inhibitors. Similarly, delivery of polynucleotides or polypeptides will be specific to particular cells and conditions.

EXAMPLES

Example I

Sequence Construction

The novel signal transduction kinase was identified after the assembly of EST sequences from a proprietary database and the public Merck Washington University EST sequence database. The initial identification of these ESTs was performed by basic local alignment search tool (BLAST) analysis of the databases using the kinase subdomain VIB sequence HRDLKPENILLD. Sequencing of two Merck Wash. U. ESTs (zb05e11, zp83b04) provided overlapping sequencing comprised of 5'UTR, open reading frame, and 3' UTR as shown in SEQ ID NO: 1. Oligonucleotide primers, sense 5'- GCCTCCATGGCCCACTCGCCGGTG-3' (SEQ ID NO:6) and antisense 5'- GGCACATGGAGCT-CATGGGTTAAGC -3' (SEQ ID NO:7), were designed based on the sequence obtained from the Merck Wash U ESTs. The primers were designed to amplify a 1353 bp fragment encompassing 6 bp upstream of the ATG initiation codon to 96 bp downstream of the TAA stop codon (SEQ ID NO:8). The described fragment was amplified using cDNA's derived from mRNA isolated from human lung, brain, and kidney tissue (Clontech, Palo Alto, Calif.), and from U937, KU812, and Jurkat cell lines using Advantage polymerase (Clontech). The PCR conditions used were: 94° C. for 1 minute followed by 20 cycles of 94° C. for 50 seconds, 65° C. for 50 seconds, 72° C. for 2 minutes. The PCR amplicons were gel purified using QiaexII agarose gel purification kit (Qiagen) and subcloned into the pCR2.1 Topo "TA" vector (Invitrogen) by the "TA" cloning approach as per the kit protocols. The topoisomerase reactions were used to transform DH5α *E. coli* competent cells (Life Technologies). Single, isolated transformed *E. coli* colonies were grown in selective media (LB broth, carbenicillin) overnight at 37° C. and subsequently used to prepare plasmid DNA (Qiagen Plasmid DNA preparation kit). Clones derived from lung, brain, and kidney cDNA's were sequenced (ABI PRISM™ Dye Terminator Cycle sequencing on ABI PRISM™377 automated sequencer). This yeilded single cDNA species of the novel kinase which validated the existence of this cDNA. A clone derived from lung cDNA was found to have sequence identical to that determined from the Merck Wash. U. EST clones. The 1353 bp sequence (SEQ ID NO:8) was found to contain a 1248 bp (SEQ ID NO:2) open reading frame (ORF) with a Kozak consensus sequence at the initiation ATG codon. Translation of the ORF resulted in a 416 amino acid protein sequence (SEQ ID NO:3) which contains all 12 conserved domains found in eukaryotic serine/threonine protein kinases. The protein has a predicted molecular weight of 46527.83 daltons, an isoelectric point of 5.097, and a net charge of −13 at pH 7.0.

Example II

Assay for Human Kinase Activity Generally

Recombinant, purified GST/kinase (10 μL) is added to 20 μg myelin basic protein (MBP) in 10 μL of a 3X kinase reaction buffer (KRB) containing: 60 mM HEPES (pH 7.5), 30 mM magnesium acetate, 0.15 mM ATP, 3 mM DTT, 0.03 mM sodium orthovanadate. The reaction is started by the addition of 5$\mu$Ci [$\gamma$-$^{32}$P] ATP (10 $\mu$L). Samples are incubated for 5 minutes at 30° C. and the reaction is stopped by addition of 4X Laemmli sample buffer. Proteins are separated on 12% Tris/glycine SDS gels, stained with Coomassie blue, dried and exposed to autoradiograph film.

Specific Assay

3x Kinase Reaction Buffer (KRB):

60 mM HEPES, pH 7.5

30 mM Magnesium Acetate

150 $\mu$M ATP 3 mM DTT 0.3 mM $Na_3VO_4$ 0.5 $\mu$g/ml Myelin Basic Protein

ASSAY:

1. Add 10 $\mu$L 3X KRB and 10 $\mu$L recombinant kinase (1 $\mu$g) to each tube.
2. Start reaction by adding 10 $\mu$L [$\gamma$-$^{32}$P] ATP (0.5 mCi/ml).
3. Incubate 30° C. for 30 minutes.
4. Stop reaction with 7.5 $\mu$L 5X Sample Buffer.
5. Boil the samples for 5 minutes then place on ice for 1 minute.
6. Load 25 $\mu$L of sample (66%) on a 10–20% Tris/glycine PAGE gel and run at 35 mA/gel for 47 minutes in Tris/glycine/SDS PAGE running buffer.
7. Stain the gel with Coomassie blue for 30–45 minutes then destain overnight in 10% methanol/7% acetic acid.
8. Fix the gel 1 hour in 3:1:6 MeOH/glacial acetic acid/$H_2O$ to reduce background radiation.
9. Photograph the gel to visualize the protein bands.
10. Dry the gel and expose to film.

Example III

Production of Anti-Kinase Polyclonal Antibodies

Antigenic peptide fragments were identified within the N-terminal, c-terminal and central regions of the novel human kinase utilizing a well established algorithm method developed by Jameson and Wolf. *The Antigenic Index: A Novel Algorithm for Predicting Antigenic Determinants*, CABIOS, 4:181 (1988). The algorithm carries out six major subroutines with the following hierarchy:

1) determination of hydrophilicity, Hopp-Woods (1981)
2) calculation of surface probability, Emini (1985)
3) prediction of backbone or chain flexibility, Karplus-Schultz (1985)
4) prediction of secondary structure, Chou-Fasman (1978)
5) prediction of secondary structure, Garnier-Robson (1978)
6) flexibility parameters and hydropathy/solvent accessibility factors are combined to determine the antigenic index The antigenic index was plotted for the entire molecule. A peptide sequence, LKQQDENNASRNQA, corresponding to SEQ ID NO:3 amino acid residue positions 364–377 was selected for synthesis and antibody production based on antigenicity and uniqueness of sequence compared to other identified kinase family members. Genosys Biotechnologies, Inc. was contracted to synthesize the peptide and produce the polyclonal antisera.

Chou, P. Y. and Fasman, G. D., (1978) Prediction of the secondary structure of proteins from their amino acid sequence, Adv. Enzyrnol, 47:45–148; Emini, E. A., Hughes, J., Perlow, D. and Boger, J., (1985) Induction of Hepatitis A Virus-Neutralizing Antibody by a Virus-Specific Synthetic Peptide, *J. Virology*, 55:836–839; Garnier, J., Osguthorpe, D. J., and Robson, B., (1978) Analysis of the accuracy and implications of simple method for predicting the secondary structure of globular proteins, *J. Mol. Biol.*, 120:97–120; Harlow, E. and Lane, D., (1988) Antibodies: A Laboratory Manual., Cold Spring Harbor Laboratory Press, Cold Spring Harbor, N.Y.; Hopp, T. P. and Woods, K. R., (1981) Prediction of Protein Antigenic Determinants from Amino Acid Sequences, Proc. Natl. Acad. Sci., 78:3824–3828; Jameson, B. A., and Wolf, H., (1988) The antigenic index: a novel algorithm for predicting antigenic determinants, CABIOS 4:181–186; Karplus, P. A. and Schultz, G. E., (1985) Prediction of chain flexibility in proteins, Naturwissenschaften, 72:212–213.

Example IV immunoprecipitation

Immunoprecipitation of the human kinase molecule described herein is performed substantially according to the method described by Suchard, S. J., et al. J. Immunol., 158:4961 (1997). Cell lysates are combined with 1 $\mu$g of either anti-enterokinase protease cleavage site/Xpress™ antibody (Invitrogen Corp.) for the recombinant kinase described herein or peptide-specific polyclonal antibody against the native kinase described herein. Rabbit IgG is used as a control. Samples are incubated at 4° C. ≧2 hours with rotation. Immunocomplexes are incubated with protein A Sepharose (Pharmacia) for 2 hours at 4° C. with rotation. The beads are washed in buffer containing 50 mM Tris (pH 8.0), 100 mM NaCl, 1 mM $Na_3VO_4$, 1% Triton X-100, and Complete™ Protease Inhibitor Cocktail. Adsorbed proteins are solubilized in sample buffer and separated on 12% SDS-PAGE minigels.

Example V

Northern Blot Analysis

A 289 bp PCR amplicon derived from the 3' end of the open reading frame and 3'UTR region of the novel cDNA (SEQ ID NO:1 base positions 1240–1528) was obtained using the primers: sense 5'- GTCTATGATAATCACAC-CTGC -3' (SEQ ID NO:9), and antisense 5'-GGCACATGGAGCTCATGGGTTAAGC -3' (SEQ ID NO:10). This DNA fragment (probe) was labeled with 50 $\mu$Ci $\alpha$-$^{32}$P-dCTP using the Ready-to-Go™ DNA Labelling Kit (Pharmacia Biotech). The labeled probe was used to hybridize against human tissue mRNA's immobilized on a solid support (Clontech Human Cancer Cell Line Multiple Tissue Northern Blot as well as a Endothelial and Epithelial Primary Cells and Cell Lines Northern Blot). Hybridization was performed essentially as described by Clontech (Protocol #PT-1200-1) using ExpressHyb™ solution. The Northern blot analysis identified a primary transcript pertaining to the novel signal transduction kinase of approximately 3.5 kb in length. Prominent transcripts are apparent primarily in immune tissues (lymph node, peripheral blood leukocytes, spleen, fetal liver, bone marrow, thymus, and placenta).

Example VI

High Throughput Screening for Compounds Which Modulate Activity

High throughput screening for modulator compounds is performed using MBP coated 96-well FlashPlates® (NEN™ Life Science Products). Kinase reaction buffer (3X kinase reaction buffer (KRB) contains: 60 mM HEPES (pH 7.5), 30 mM magnesium acetate, 0.15 mM ATP, 3 mM DTT, 0.03 mM sodium orthovanadate) 0.25 $\mu$Ci [$\gamma^{33}$P]-ATP at a concentration no greater than 1 $\mu$g/ml, (determined by titration of individual enzyme preparations for a concentration that allows kinetic determinations over a 1 hour time course of the human kinase) are added to each well and incubated 1 hour at 30° C. in the presence or absence of 10 μM test compound. Total reaction volume is 100 μL. Following incubation, the reaction mixture is aspirated and the wells rinsed 2 times with 300 μL PBS. Incorporation of raiolabeled phosphate is determined by scintillation counting, Packard Instrument Co. TopCount, 12-detector, 96-well microplate scintillation counter and luminescence counter, model B991200. Compounds which inhibit kinase activity ≧50 percent at 10 μM are are indicated by a >50% reduction in scintillation counts. Specificity and selectivity studies is determined by titration of inhibitory compounds to determine the $IC_{50}$ (or other standard quantitation well known in the art for comparison) and by the substitution of other kinases in the assay. For example, determination of relative inhibitory activity of the kinase in comparison to recombinant SOK-1 and/or mst-3, expressed and isolated in a similar manner, assayed under similar conditions, provides selectivity data.

Example VII

High Throughput Screening Protocol

Test compounds Test compounds are prepared in advance from 2.5 mg/ml stock solutions in DMSO by diluting 1:10 in distilled water and then 1:10 again. Ten (10) μl of the 1:100 dilution solutions (25 μg/ml in 1% DMSO) are prepared in 96 well Microlite 1 plates (Dynatech) and plates are stored at −20° C. until the evening prior to the start of the assay.

Control plates A plate containing control solutions is included in each run of the screen for QA purposes. Such plates are prepared at the beginning of the HTS campaign and stored at −20° C. until required. Zero inhibition (MAX. signal) wells (columns 3, 6, 8 and 10) contain 10 μl of 1% (v/v) DMSO solution in MilliQ water. 100% inhibition (MIN signal) wells (columns 1, 4, 9 and 11) contain 10 μl of 220 nM ZM333141/1 in 1% DMSO solution in MilliQ water. 50% inhibition (REF. signal) wells (columns 2, 5, 7 and 12) contain a reference compound at a concentration known to provide approximately 50% inhibition in 1% (v/v) DMSO solution in MilliQ water.

Assay Components (1) recombinant kinase (expressed in *E. coli* or eukaryotic cells as described herein) or a lysate of a prokaryotic or eukaryotic cell expressing recombinant enzyme, or the natural enzyme partially purified from a human cell line.

(2) [γ-$^{33}$-P]-adenosine triphosphate (3) myelin basic protein linked to the surface of PVT SPAN beads (purchased from Amersham International) by an antibody-protein A or other appropriate method.

To Microlite I plates containing 10 μl of test compound, which have been left on the bench overnight to reach room temperature, 25 ml of GST-Rb/ATP/$ATP^{33}$ is added, immediately followed by 20 μl of Enzyme, using two Multidrops. The plates are stacked in 13 plate stacks (with an empty plate on top of each stack to minimise evaporation from the top plate) and left at room temperature for 105 minutes. 150 μl of "Stop Solution" containing beads antibody and EDTA is added using a Multidrop. The plates are sealed with Topseal-S plate sealers and left on the bench overnight, surrounded by Scotlab perspex screens. The plates are then centrifuged (Heraeus Megafuge 3.0R) at 2500 rpm, 1124xg., for 5 minutes (2 plates per trunnion) and counted on a Topcount (I4.34); (isotop: $P^{33}$; counting time: 20 seconds/well).

The data may be analysed using well-known software systems. A threshold for inhibition is set, e.g., 60% inhibition of scintillation signal. Compounds reaching the inhibition threshold are scored as active.

Example VIII

PCR of SEQ ID NO:1 from Various Human Cdnas of Hematopoietic Origin

SEQ ID NO:1 message is determined to be present in other cells of hematopoictic orign by PCR with cDNA's isolated from different cell-lines of hematopoietic orign.

Target product was amplified from 2–2.5 ng of reverse transcribed mRNAs in a 20 μL reaction using Advantage™ KlenTaq polymerase (Clontech # 8417-1, lot 7020348) according to the manufacturer's recommendations. Primer set sequences are sense 5'-GTCTATGATAATCACACCTGC -3' (SEQ ID NO:9), and antisense 5'-GGCACATGGAGCTCATGGGTTAAGC -3' (SEQ ID NO:10). A 289 bp PCR amplicon indicative of expression of the novel kinase is generated derived from the 3' end of the open reading frame and 3'UTR region of the novel CDNA (SEQ ID NO:1 base positions 1240–1528). The PCR conditions used are: 94° C. for 1 minute followed by 20 cycles of 94° C. for 50 seconds, 65° C. for 50 seconds, 72° C. for 2 minutes. 10 μL of each reaction is analyzed on a 1% agarose gel containing 0.5 μg/mL final concentration ethidium bromide in TAE buffer as in Sambrook et al., Molecular Cloning Lab Manual, Second Edition, Cold Spring Harbor Press (1989), using 600 ng of 1 kb DNA ladder as markers (Life Technologies, cat # 15615-016).

Example IX

Expression and Purification of Gst/Human Signal Transduction Kinase Fusion Protein A single, isolated, BL21 transformed clone was grown overnight in 10 mL Lennox L broth (LB broth containing 50 mg/ml carbenicillin) and then seeded into 1 liter LB broth/carbenicillin and grown at 37° C. with shaking (225 rpm) to an $A_{600}$ of 0.5–0.8. Expression of GST/kinase fusion protein was induced by adding isopropylthio-β-galactoside to 100 mM and continuing the incubation for 2 additional hours. Following incubation, the cells were centrifuged 1500 x g for 10 min at 4° C., resuspended in 50 mL phosphate buffered saline (PBS) containing Complete™ Protease Inhibitor Cocktail (Boehringer Mannheim GmbH), then lysed by sonication on ice. Triton X-100 was added to the sonicate to a final concentration of 1% to aid in the solubilization of the fusion protein. Cellular debris was removed by centrifugation (12,000 x g, 4° C.) and the supernatant was used as the source for obtaining purified GST/kinase.

Purification of Gst/Kinase Fusion Protein

GST/kinase was purified by Glutathione Sepharose 4B beads (Pharmacia) affinity column chromatography using a 1 ml gravity fed open column. The suspension was allowed to pass through the column then the column was washed three times with PBS containing protease inhibitors. Finally, the GST-kinase fusion protein was eluted from the column by the addition of 1 mL elution buffer (10 mM reduced glutathione in 50mM Tris-HCl, pH 8.0 with protease inhibitors). The GST/kinase was stored in aliquots at −20° C. until needed.

Example X

Dominant Negative/Inactive Kinase Mutant

A dominant negative/inactive kinase mutant, for example, can readily be produced with the tools provided herein to further produce one embodiment exemplified herein by changing the lysine at SEQ ID NO:3 position 53 to an arginine. This mutation has been shown to produce inactive and/or dominant negative kinases for numerous other serine/threonine kinases. See, e.g., Hanks, S. K., et al. Science, 241:42 (1988). A dominant negative or inactive kinase mutant of the novel kinase was produced by changing the lysine at position 53 to an arginine. The mutation was introduced into the novel kinase/pCR2.1 construct using the Quick Change Site Directed Mutagenesis Kit (Stratagene) and the oligonucleotides 5'-CAGCAAGTCGTTGCTATCCGGATCATAGACCTTG-AG -3' (sense) (SEQ ID NO:13) and 5'-CTCAAGGTCTATGATCCGGATAGCAACGACTTGC-TG -3' (antisense) (SEQ ID NO: 14). This produced the construct K53R/pCR2.1. Epitope tagged dominant negative vector construction: A constitutive expression construct containing the novel kinase K53R dominant negative kinase CDS was produced using pcDNA3.1His (Invitrogen Corporation). This expression construct is designed to express an N-terminal epitope tagged fusion protein containing the following protein sequence: Methionine - (Histidine)$_6$ - Enterokinase protease cleavage site/Xpress™ antibody epitope - novel kinase K53R dominant negative kinase protein. The novel kinase K53R cDNA was excised from the K53R/pCR2.1 construct using EcoRI (5') and EcoICRI (3') and inserted into the pcDNA3.1His vector using EocRI (5') and EcoRV (3') restriction endonuclease sites at the 5' end and 3' end, respectively.

Example XI

Activation of Transcription Factors by TEN-1 Kinase

Shown below is the general format of the transcription activation reporter assays used to determine if the signal transduction kinase (SEQ ID NO:3) activates specific transfactors. The PathDetect™ System (including reporter constructs and positive control constructs) was used to perform these assays. Stratagene, La Jolla, Calif. All assays were performed in triplicate and repeated several separate times.

1. The cells were diluted to $1.5\times10^5$/ml and 2 ml ($3\times10^5$ cells) were plated into each well of 6-well dishes
2. The cells were cultured overnight at 37° C., 5% $CO_2$, 90% relative humitidity (these conditions were used throughout the assay
3. Cells were transfected using Stratagene's Lipotaxi reagent according to the protocol supplied with the reagent. The protocol is as follows (described for 3 transfections)
4. Combine 840 $\mu$l DMEM+60 $\mu$l Lipotaxi reagent in a polystyrene tube
5. Add DNA's (see table) to the DMEM/Lipotaxi solution
6. Incubate for 15–30 minutes at room temperature
7. Add 2.1 ml DMEM to the DMEM, Lipotaxi, DNA solution
8. Remove the culture media from the cells
9. Add 1 ml of the Lipid/DNA solution to each well of cells in a drop wise fashion while swirling the dish
10. Incubate the Lipid/DNA:cell cutlure for 5–7 hours at 37° C. in 5% $CO_2$
11. Add lml DMEM/1% FBS and culture overnight
12. Replace the media with fresh DMEM/0.5% FBS and culture overnight
13. Test the cells for luciferase activity using Packard's Luc-Lite kit reagents and protocol as follows
14. Remove the media from the cells and add 300 $\mu$l of Luc-Lite reagent that was previously diluted 1:1 with PBS containing 1 mM $CaCl_2$ and $MgCl_2$
15. Incubate at room temperature for 10 minutes
16. Dispense 200 $\mu$l of the cell lysate into white plastic 96-well plates and read the light emission on a Perkin-Elmer/Tropix 96-well Flourimeter Table of DNA's used in a PathDetect ™ assay (TEN1 = SEQ ID NO:3)

| Reporter Vector @ 1 $\mu$g/well | Positive Control Vector, @ 50 ng/well | Kinase Expression Vector @ 50 ng, 250 ng, 500 ng, 750 ng/well | Expression Vector w/o Insert @ 50 ng, 250ng, 500 ng, 750 ng/well | Carrier Vector DNA @ 1 $\mu$g/well |
|---|---|---|---|---|
| pX-Luc, 3 $\mu$g, 3 $\mu$l | — | — | — | 3 $\mu$g, 3 $\mu$l |
| pX-Luc, 3 $\mu$g, 3 $\mu$l | — | — | pIRES-EGFP, 150 ng, 3 $\mu$l | 2.85 $\mu$g, 2.85 $\mu$l |
| pX-Luc, 3 $\mu$g, 3 $\mu$l | — | — | pIRES-EGFP, 750 ng, 3 $\mu$l | 2.25 $\mu$g, 2.25 $\mu$l |
| pX-Luc, 3 $\mu$g, 3 $\mu$l | — | — | pIRES-EGFP, 1500 ng, 3 $\mu$l | 1.5 $\mu$g, 1.5 $\mu$l |
| pX-Luc, 3 $\mu$g, 3 $\mu$l | — | — | pIRES-EGFP, 2250 ng, 3 $\mu$l | 0.75 $\mu$g, 0.75 $\mu$l |
| pX-Luc, 3 $\mu$g, 3 $\mu$l | — | TEN1#1/ pIRES-EGFP, 150 ng, 3 $\mu$l | — | 2.85 $\mu$g, 2.85 $\mu$l |
| pX-Luc, 3 $\mu$g, 3 $\mu$l | — | TEN1#1/ pIRES-EGFP, 750 ng, 3 $\mu$l | — | 2.25 $\mu$g, 2.25 $\mu$l |
| pX-Luc, 3 $\mu$g, 3 $\mu$l | — | TEN1#1/ pIRES-EGFP, 1500 ng, 3 $\mu$l | — | 1.5 $\mu$g, 1.5 $\mu$l |
| pX-Luc, 3 $\mu$g, 3 $\mu$l | — | TEN1#1/ pIRES-EGFP, 2250 ng, 3 $\mu$l | — | 0.75 $\mu$g, 0.75 $\mu$l |
| pX-Luc, 3 $\mu$g, 3 $\mu$l | pFC-X, 150 ng, 6 $\mu$l | | — | 2.85 $\mu$g, 2.85 $\mu$l |

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A purified polypeptide comprising the amino acid sequence as depicted in SEQ ID NO:3 or a variant of SEQ ID NO:3 having at least about 90% identity to a member selected from the group consisting of: (SEQ ID NO:3, SEQ ID NO:3 positions 24–274, and SEQ ID NO:3 positions 275–416).

2. A method of identifying compounds that modulate a biological and/or pharmacological activity of a signal transduction kinase polypeptide, comprising:

(a) combining a candidate compound modulator with a polypeptide according to claim 1, and (b) measuring an effect of the candidate compound modulator on the biological and/or pharmacological activity of the polypeptide.

3. A method of identifying compounds that modulate a biological and/or pharmacological activity of a signal transduction kinase polypeptide according to claim 2, comprising:

(a) combining a candidate compound modulator with a host-cell which expresses said polypeptide, and (b) measuring an effect of the candidate compound modulator on the biological and/or pharmacological activity of the polypeptide.

* * * * *